(12) United States Patent
Kawagishi et al.

(10) Patent No.: US 8,932,225 B2
(45) Date of Patent: Jan. 13, 2015

(54) ULTRASONIC DIAGNOSTIC APPARATUS AND ULTRASONIC DIAGNOSTIC METHOD

(75) Inventors: Tetsuya Kawagishi, Nasushiobara (JP); Hiroyuki Ohuchi, Nasushiobara (JP); Takeshi Sato, Nasushiobara (JP); Makoto Hirama, Otawara (JP); Tomohisa Imamura, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1607 days.

(21) Appl. No.: 11/627,667

(22) Filed: Jan. 26, 2007

(65) Prior Publication Data

US 2007/0197916 A1    Aug. 23, 2007

(30) Foreign Application Priority Data

Jan. 26, 2006   (JP) ................. 2006-017772

(51) Int. Cl.
| | | |
|---|---|---|
| *A61B 8/00* | (2006.01) | |
| *A61B 8/06* | (2006.01) | |
| *A61B 8/08* | (2006.01) | |
| *G01S 7/52* | (2006.01) | |
| *G01S 15/89* | (2006.01) | |

(52) U.S. Cl.
CPC . *A61B 8/463* (2013.01); *A61B 8/06* (2013.01); *A61B 8/481* (2013.01); *G01S 7/52074* (2013.01); *G01S 15/8927* (2013.01); *G01S 15/8952* (2013.01); *G01S 7/52046* (2013.01)
USPC ............ 600/443; 600/407; 600/437; 600/441

(58) Field of Classification Search
USPC .......... 600/437–440, 443–449; 367/162–163; 73/584, 596–604, 627–630
See application file for complete search history.

(56) References Cited

U.S. PATENT DOCUMENTS

| | | | |
|---|---|---|---|
| 6,783,496 B2 * | 8/2004 | Hao et al. ...................... | 600/458 |
| 2004/0030253 A1 * | 2/2004 | Brock-Fisher et al. ........ | 600/458 |

FOREIGN PATENT DOCUMENTS

JP          8-182680         7/1996

* cited by examiner

*Primary Examiner* — Mark Remaly
(74) *Attorney, Agent, or Firm* — Oblon, Spivak, McClelland, Maier & Neustadt, L.L.P

(57) ABSTRACT

An ultrasonic diagnostic apparatus comprises a first reception echo obtaining unit, a second reception echo obtaining unit, a reception echo combining unit, and an image generating unit. The first reception echo obtaining unit transmits a plurality of ultrasonic pulses having frequency spectra different from one another to an object, and obtains each of reception echoes corresponding to the plurality of ultrasonic pulses. The second reception echo obtaining unit transmits an ultrasonic pulse having the same frequency component characteristics as an combined pulse obtained by combining the plurality of ultrasonic pulses, and to obtain an reception echo. The reception echo combining unit combines the reception echoes obtained by the first reception echo obtaining unit and the reception echo obtained by the second reception echo obtaining unit to generate a combined signal. The image generating unit generates an image of echoes reflected from the object on the basis of the combined signal.

28 Claims, 17 Drawing Sheets

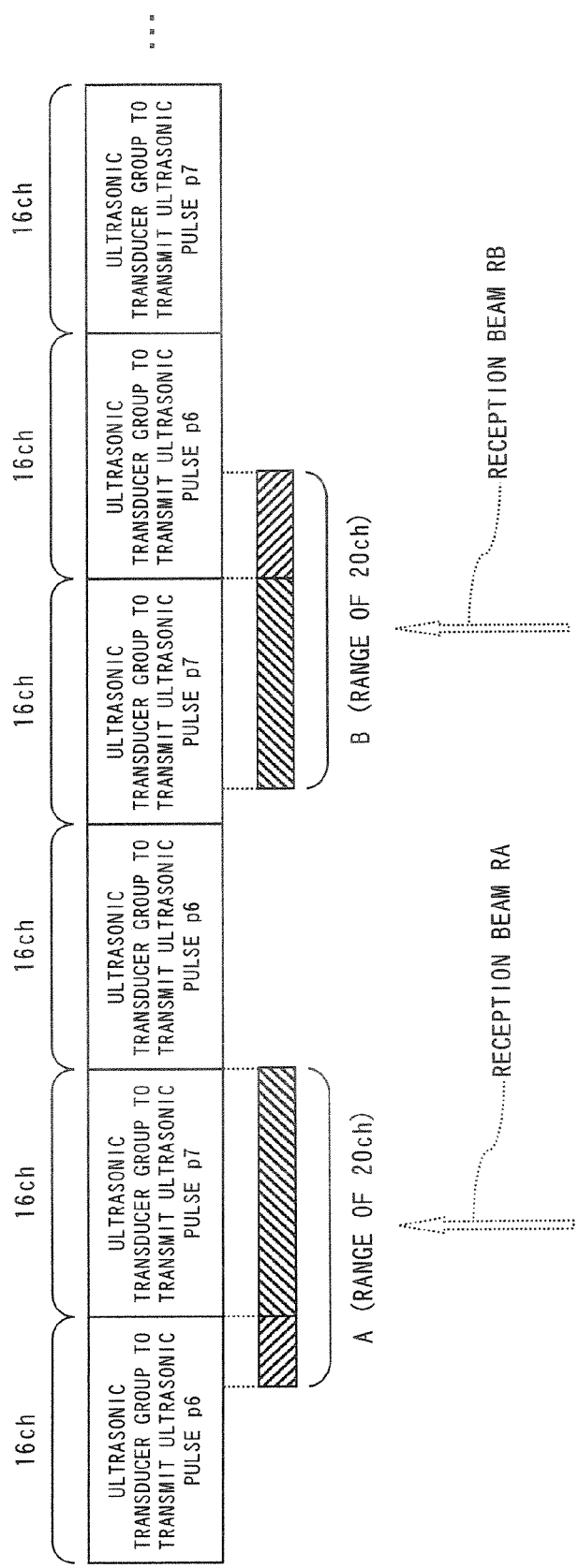
F I G. 26

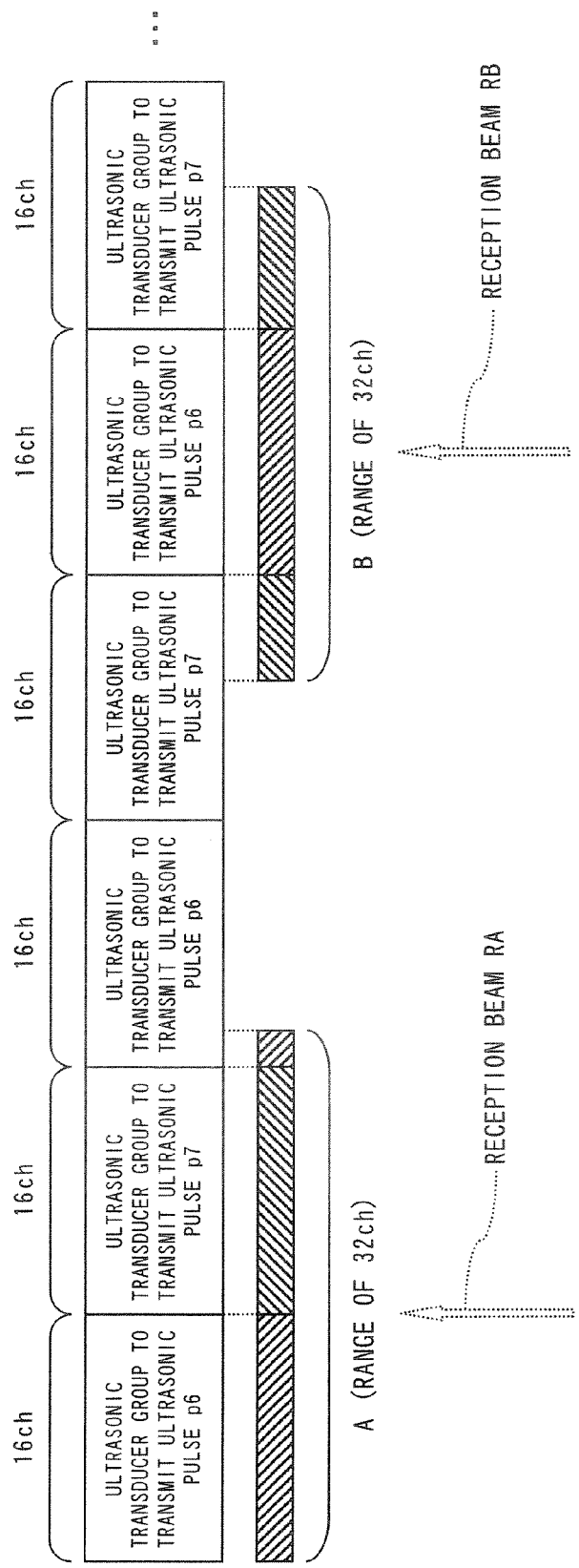
F I G. 27

ULTRASONIC DIAGNOSTIC APPARATUS AND ULTRASONIC DIAGNOSTIC METHOD

BACKGROUND OF THE INVENTION

1. Field of the Invention

The present invention relates to ultrasonic diagnostic apparatuses and ultrasonic diagnostic method that obtain biological information of an object by irradiating ultrasonic pulses into the object, receiving ultrasonic echoes generated in the object, and performing various processing operations. In particular, the present invention relates to an ultrasonic diagnostic apparatus and an ultrasonic diagnostic method capable of performing imaging according to a contrast echo method using a contrast medium.

2. Description of the Related Art

Ultrasonic diagnostic apparatuses are apparatuses that obtain biological information, such as tomographic images of tissues of a living body in an object and blood flow images, by irradiating ultrasonic pulses into the object from piezoelectric transducers (ultrasonic transducers) included in an ultrasonic probe, receiving ultrasonic echoes generated in the object with the piezoelectric transducers, and performing various processing operations on the received ultrasonic echoes.

An imaging method employed by such ultrasonic diagnostic apparatuses is an imaging method referred to as a contrast echo method. In the contrast echo method, microbubbles are injected into the blood vessel of the object as a contrast medium to enhance the scattering ultrasonic echoes. More specifically, in imaging according to the contrast echo method, ultrasonic pulses having predetermined frequency spectra are irradiated, and nonlinear components of the ultrasonic echoes reflected from the microbubbles as the contrast medium, are used for visualization.

However, in an imaging technique according to a known contrast echo method, only some of the bubbles injected into the object contribute to the visualization. This is because, when the frequency of the ultrasonic pulses to be irradiated is kept constant, the signal strength of the nonlinear components included in the ultrasonic echoes strongly depends on the radiuses of the bubbles. That is, since the resonant frequencies of the bubbles differ depending on the radiuses thereof, only some of the bubbles having radiuses that are resonant with the frequencies of the transmitted ultrasonic pulses are utilized for the visualization.

Thus, it is desirable to obtain ultrasonic echoes reflected from more bubbles having different radiuses so as to visualize images from the aspect of sensitivity.

On the other hand, the transmitted ultrasonic pulses undesirably destroy some of the bubbles. Accordingly, in the imaging according to the contrast echo method, the significantly low intensity ultrasonic pulses, having amplitude only one-tenth of the ultrasonic pulses normally used for non-contrast imaging, are used for the imaging. Thus, there may be a problem that the sensitivity is insufficient for, particularly, regions deep within the object. In particular, in low MI (mechanical index) mode imaging that uses ultrasonic pulses having low sound pressure in order not to destroy the bubbles, the sensitivity is actually insufficient.

In addition, a technique that uses second harmonic components for the visualization as nonlinear components included in ultrasonic echoes reflected from bubbles has been developed. However, in this technique, tissue harmonic components reflected from tissues of a living body are also visualized, which undesirably makes it difficult to see blood flow contrast images enhanced by the bubbles.

SUMMARY OF THE INVENTION

The present invention has taken into consideration the above-described problems, and it is an object of the present invention to provide an ultrasonic diagnostic apparatus and an ultrasonic diagnostic method, recognition of a contrast enhancement by bubbles is allowed easy at a higher sensitivity.

In addition, the present invention has taken into consideration the above-described problems, and it is an object of the present invention to provide an ultrasonic diagnostic apparatus and an ultrasonic diagnostic method, a motion artifact of an ultrasonographic image can be reduced.

In addition, the present invention has taken into consideration the above-described problems, and it is an object of the present invention to provide an ultrasonic diagnostic apparatus and an ultrasonic diagnostic method, a signal strength of a bubble echo can be increased, whereas a signal strength of a tissue echo can be reduced.

In addition, the present invention has taken into consideration the above-described problems, and it is an object of the present invention to provide an ultrasonic diagnostic apparatus and an ultrasonic diagnostic method, an intensity of vertical lines appeared on the ultrasonographic image can be decreased.

To solve the above-described problems, an ultrasonic diagnostic apparatus in one aspect comprises: a first reception echo obtaining unit configured to transmit a plurality of ultrasonic pulses having frequency spectra different from one another to an object, and to obtain each of reception echoes corresponding to the plurality of ultrasonic pulses; a second reception echo obtaining unit configured to transmit an ultrasonic pulse having the same frequency component characteristics as an ultrasonic pulse obtained by combining the plurality of ultrasonic pulses, and to obtain an reception echo; a reception echo combining unit configured to combine the reception echoes obtained by the first reception echo obtaining unit and the reception echo obtained by the second reception echo obtaining unit to generate a combined signal; and an image generating unit configured to generate an image of echoes reflected from the object on the basis of the combined signal.

To solve the above-described problems, an ultrasonic diagnostic method in one aspect comprises: obtaining first reception echoes for transmitting a plurality of ultrasonic pulses having frequency spectra different from one another to an object, and for obtaining each of reception echoes corresponding to the plurality of ultrasonic pulses; obtaining second reception echoes for transmitting an ultrasonic pulse having the same frequency component characteristics as an combined pulse obtained by combining the plurality of ultrasonic pulses, and to obtain an reception echoes; generating reception echoes for combining the reception echoes obtained by the step of obtaining first reception echoes and the reception echoes obtained by the step of obtaining second reception echoes to generate a combined signal; and generating an image for generating an image of echoes reflected from the object on the basis of the combined signal.

Therefore, according to the present invention to provide the ultrasonic diagnostic apparatus and the ultrasonic diagnostic method, recognition of a contrast enhancement by bubbles is allowed easy at a higher sensitivity.

In addition, according to the present invention to provide the ultrasonic diagnostic apparatus and the ultrasonic diagnostic method, a motion artifact of an ultrasonographic image can be reduced.

In addition, according to the present invention to provide the ultrasonic diagnostic apparatus and the ultrasonic diagnostic method, a signal strength of a bubble echo can be increased, whereas a signal strength of a tissue echo can be reduced.

In addition, according to the present invention to provide the ultrasonic diagnostic apparatus and the ultrasonic diagnostic method, the intensity of vertical lines appeared on the ultrasonographic image can be decreased.

BRIEF DESCRIPTION OF THE DRAWINGS

In the accompanying drawings:

FIG. 26 is a diagram illustrating a method for transmitting the ultrasonic pulses employed by the ultrasonic diagnostic apparatus shown in FIG. 25;

FIG. 27 is a diagram illustrating a method for transmitting the ultrasonic pulses employed by the ultrasonic diagnostic apparatus shown in FIG. 25.

DESCRIPTION OF THE PREFERRED EMBODIMENTS

An ultrasonic diagnostic apparatus and an ultrasonic diagnostic method according to embodiments of the present invention will be described with reference to the accompanying drawings.

Figure 1:
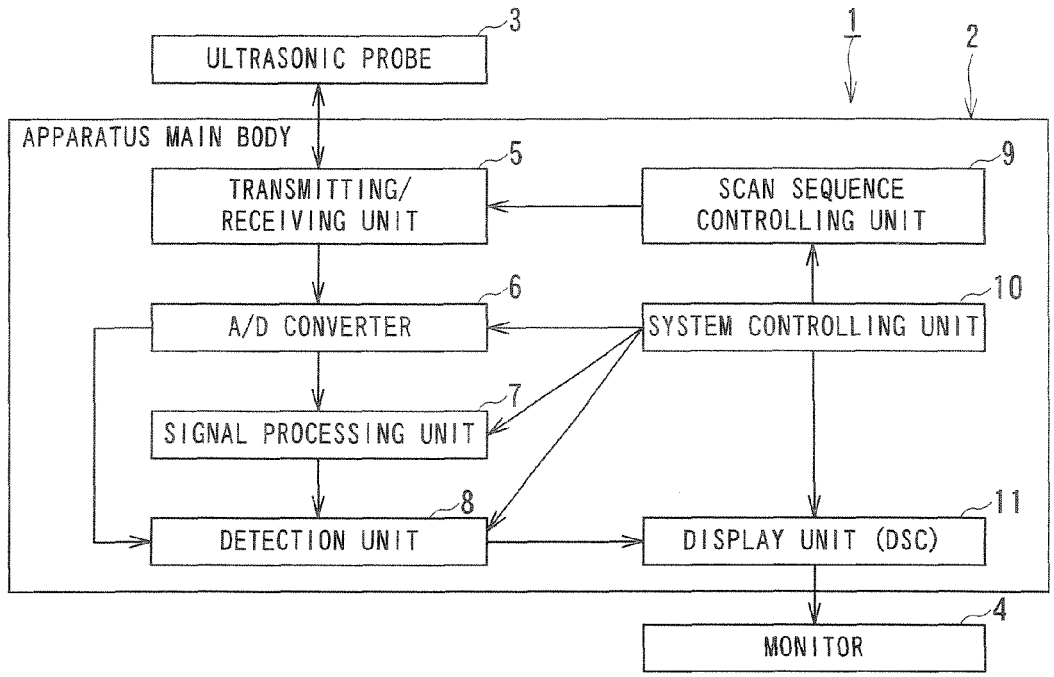
FIG. 1 is a configuration diagram showing an ultrasonic diagnostic apparatus according to a first embodiment of the present invention.

FIG. 1 is a configuration diagram showing an ultrasonic diagnostic apparatus according to a first embodiment of the present invention.

An ultrasonic diagnostic apparatus 1 according to the first embodiment is constituted by an apparatus main body 2, an ultrasonic probe 3, and a monitor 4. The apparatus main body 2 has a transmitting/receiving unit 5, an A/D (analog to digital) converter 6, a signal processing unit 7, a detection unit 8, a scan sequence controlling unit 9, a system controlling unit 10, and a display unit 11. Each unit in the apparatus main body 2 may be implemented by circuits or by a CPU (central processing unit) of a computer loading a control program.

The ultrasonic probe 3 has a plurality of ultrasonic transducers. Each ultrasonic transducer transmits ultrasonic pulses into an object (not shown) after converting transmission signals, applied by the transmitting/receiving unit 5 as electric pulses, into the ultrasonic pulses. In addition, each of the ultrasonic transducers has a function to supply reception echoes, i.e., electronic signals, to the transmitting/receiving unit 5 after receiving ultrasonic echoes caused by the ultrasonic pulses having transmitted into the object.

The transmitting/receiving unit 5 has a function to supply the transmission signals to each ultrasonic transducer of the ultrasonic probe 3 according to a control signal fed by the scan sequence controlling unit 9 as a scan sequence signal, thereby controlling the ultrasonic probe 3 so that the ultrasonic pulses having predetermined characteristics are transmitted from the ultrasonic probe 3. In addition, the transmitting/receiving unit 5 has a function to receive reception echoes from the ultrasonic probe 3, to perform predetermined preprocessing, such as delay and phased addition, and to supply the processed reception echoes to the A/D converter 6.

The scan sequence controlling unit 9 has a function to control the transmitting/receiving unit 5 by supplying the control signal to the transmitting/receiving unit 5 as the scan sequence signal so that the ultrasonic pulses having predetermined frequency spectra (frequency components) are transmitted from the ultrasonic probe 3. More specifically, the scan sequence controlling unit 9 has a function to control the transmitting/receiving unit 5 by supplying the control signal to the transmitting/receiving unit 5 so that a plurality of ultrasonic pulses, having a plurality of frequency spectra at least one of whose center frequency, amplitude, and frequency band differ from those of the other spectra, are sequentially transmitted from the ultrasonic probe 3. In addition, the scan sequence controlling unit 9 can cause the plurality of ultrasonic pulses to be sequentially transmitted while differing at least one of a phase, a transmission aperture, and a transmission focus for each of the plurality of ultrasonic pulses.

In particular, the scan sequence controlling unit 9 sets the scan sequence so that the plurality of the ultrasonic pulses having different frequency spectra and a ultrasonic pulse, having the same frequency component characteristics as the ultrasonic pulse obtained by performing a linear operation to combine the plurality of pulses, are sequentially transmitted.

The A/D converter 6 has a function to supply digital reception echoes to the signal processing unit 7 or the detection unit 8 after digitalizing the analog reception echoes received from the transmitting/receiving unit 5.

The signal processing unit 7 has a function to perform signal processing on the reception echoes received from the A/D converter 6. The signal processing unit 7 also has a function to supply a combined signal obtained by the signal processing to the detection unit 8. More specifically, the signal processing unit 7 performs the signal processing so as to combine the reception echoes corresponding to the ultrasonic pulses each having a different frequency spectrum and generate the combined signal.

The detection unit 8 obtains the necessary pulse signals or reception echoes from the signal processing unit 7 or the A/D converter 6, has a function to perform envelope detection on the obtained pulse signals or reception echoes, and to supply the detection result to the display unit 11 as a detection signal. In particular, the detection unit 8 obtains the pulse signals from the signal processing unit 7 for generation of a contrast image using microbubbles according to a contrast echo method, and generates the detection signal. The detection unit 8 also obtains predetermined reception echoes from the A/D converter 6 for generation of a tissue (B-mode) image, which becomes a background image of the contrast image, and generates the detection signal.

It may be come from behind placement of the signal processing unit 7 and the detection unit 8. In that case, the detection unit 8 obtains the necessary reception echoes from the A/D converter 6, and performs envelope detection on the obtained reception echoes. In addition, the signal processing unit 7 performs signal processing on the reception echoes received from the detection unit 8.

The display unit 11 has a DSC (digital scan converter). The display unit 11 has a function to generate a video signal used for displaying an image on the monitor from the detection signal received from the detection unit 8, and to supply the generated video signal to the monitor 4 to cause the monitor 4 to display the image. The DSC of the display unit 11 converts the scan mode of the detection signal received from the detection unit 8 from an ultrasonic scan mode into a television scan mode for displaying.

The system controlling unit 10 has a function to entirely control each unit in the apparatus main body 2 by supplying control signals to the transmitting/receiving unit 5, the A/D converter 6, the signal processing unit 7, the detection unit 8, and the scan sequence controlling unit 9.

An operation of the ultrasonic diagnostic apparatus 1 will be described next.

Figure 2:
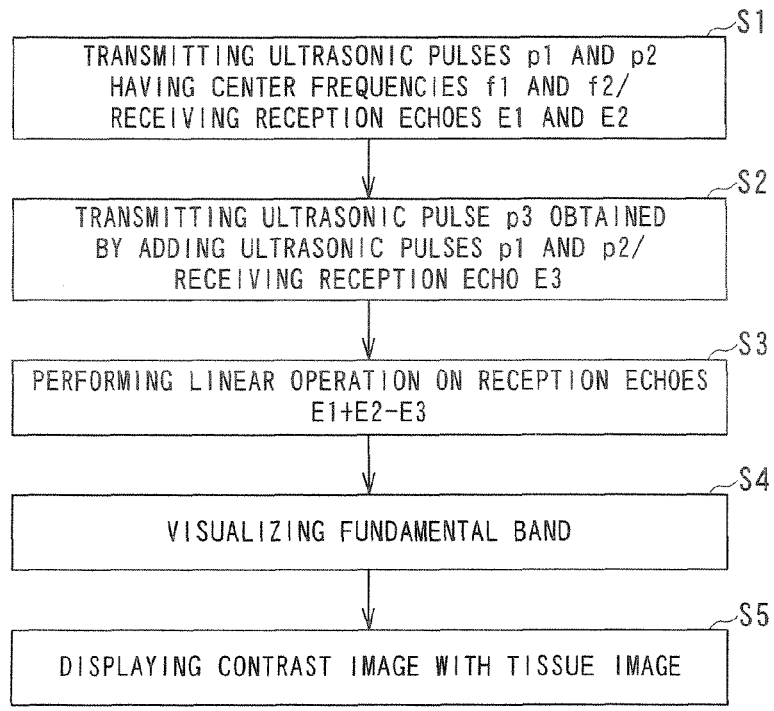
FIG. 2 is a flowchart showing a procedure that the ultrasonic diagnostic apparatus shown in FIG. 1 performs when visualizing a blood flow according to a contrast echo method using microbubbles as a contrast medium.

FIG. 2 is a flowchart showing a procedure that the ultrasonic diagnostic apparatus 1 shown in FIG. 1 performs when visualizing the blood flow according to the contrast echo method using microbubbles as a contrast medium. An alphabet "S" followed by a numeral in the figure represents each step of the flowchart.

Firstly, the contrast medium including microbubbles is injected to the object. Many microbubbles having various radiuses are then inducted to an imaging target part such as a blood vessel.

At step S1, for example, ultrasonic pulses p1 and p2 having different center frequencies f1 and f2 are transmitted to the imaging target part of the object from the ultrasonic probe 3 at different timings. The ultrasonic probe 3 then receives ultrasonic echoes, which are caused by the microbubbles at the imaging target part, and the signal processing unit 7 obtains the ultrasonic echoes as reception echoes E1 and E2, respectively.

More specifically, the scan sequence controlling unit 9 generates a scan sequence signal so that the ultrasonic pulse p1 having the center frequency f1 and the ultrasonic pulse p2 having the center frequency f2 are sequentially transmitted from the ultrasonic probe 3 at regular intervals. At this time, the center frequency f2 is set at a value different from the center frequency f1.

The scan sequence controlling unit 9 supplies the generated scan sequence signal to the transmitting/receiving unit 5. This causes the transmitting/receiving unit 5 to generate transmission signals according to the scan sequence signal received from the scan sequence controlling unit 9, and to supply the generated transmission signals to each of ultrasonic transducers of the ultrasonic probe 3. Accordingly, each of the ultrasonic pulse p1 having the center frequency f1 and the ultrasonic pulse p2 having the center frequency f2 (f2≠f1) is transmitted to the imaging target part of the object.

Since many microbubbles having different radiuses exist at the imaging target part, the ultrasonic echoes, which are caused by the ultrasonic pulses reflecting from the microbubbles and tissues, are received by the ultrasonic probe 3. The ultrasonic echoes, corresponding to two ultrasonic pulses p1 and p2, received by the ultrasonic probe 3 are converted into the reception echoes E1 and E2, i.e., the electric signals, and are sequentially supplied to the transmitting/receiving unit 5.

The transmitting/receiving unit 5 sequentially supplies each of the reception echoes E1 and E2, received from the ultrasonic probe 3, to the A/D converter 6. The A/D converter 6 converts the analog reception echoes E1 and E2 supplied from the transmitting/receiving unit 5 into digital reception echoes E1 and E2, respectively. The A/D converter 6 sequentially supplies each of the digitalized reception echoes E1 and E2 to the signal processing unit 7.

The signal processing unit 7 performs predetermined processing, such as delay and phased addition, on each of the reception echoes E1 and E2 received from the A/D converter 6. The signal processing unit 7 then temporarily stores the reception echoes E1 and E2 corresponding to two kinds of transmitted ultrasonic pulses p1 and p2, respectively.

Figure 3:
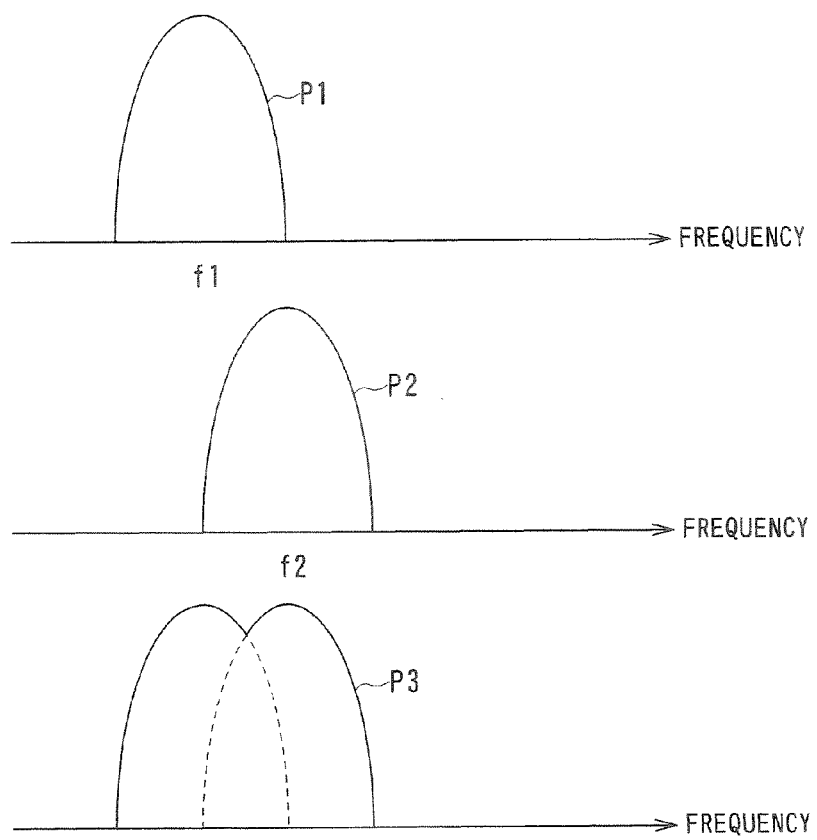
FIG. 3 is a schematic diagram showing an example of frequency spectra for a plurality of ultrasonic pulses to be sequentially transmitted from an ultrasonic probe of the ultrasonic diagnostic apparatus shown in FIG. 1.
Figure 4:
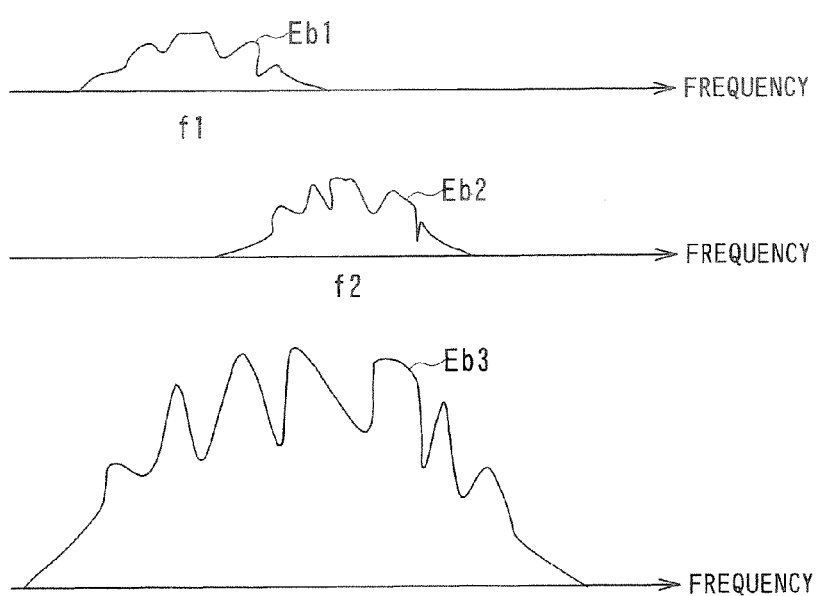
FIG. 4 is a schematic diagram showing an example of frequency spectra for reception echoes from bubbles obtained by transmitting each of ultrasonic pulses shown in FIG. 3.

FIG. 3 is a schematic diagram showing an example of frequency spectra for a plurality of ultrasonic pulses to be sequentially transmitted from the ultrasonic probe 3 of the ultrasonic diagnostic apparatus 1 shown in FIG. 1. FIG. 4 is a schematic diagram showing an example of frequency spectra for reception echoes from the bubbles obtained by transmitting each of the ultrasonic pulses shown in FIG. 3.

Horizontal axes of FIGS. 3 and 4 represent a frequency. As shown in FIG. 3, the ultrasonic pulse p1 has an ultrasonic spectrum centered at the center frequency f1, whereas the ultrasonic pulse p2 has an ultrasonic spectrum centered at the center frequency f2. Each of the ultrasonic pulses p1 and p2 is sequentially transmitted to the microbubbles in the object from the ultrasonic probe 3.

The microbubbles existing at the imaging target part have different radius values. Nonlinear signal components are obtained from the microbubbles having radiuses that are resonant with each frequency spectrum of the transmitted ultrasonic pulses in a broad frequency band including a fundamental band. That is, by setting the center frequency of each of the ultrasonic pulses to be transmitted at a different value and shifting each frequency spectrum, the nonlinear components can be obtained from the microbubbles having more kinds of radiuses in the broad frequency band including the fundamental band.

Accordingly, as shown in FIG. 4, bubble echoes Eb1 and Eb2, which are the nonlinear components obtained from the microbubbles, in the reception echoes E1 and E2 have frequency spectra centered at the center frequencies f1 and f2, which are different from each other. On the other hand, it is considered that tissue echoes Ec1 and Ec2, which are clutter components obtained from a tissue of a living body, in the reception echoes E1 and E2 are substantially linear components in the fundamental band.

Then, at step S2, an ultrasonic pulse p3, obtained by adding the ultrasonic pulses p1 and p2, is transmitted from the ultrasonic probe 3. The signal processing unit 7 then obtains a reception echo E3. Transmission of the ultrasonic pulse p3 and acquisition of the reception echo E3, like the transmission of the ultrasonic pulses p1 and p2 and the acquisition of the reception echoes E1 and E2, are performed under the control of the scan sequence controlling unit 9.

That is, the ultrasonic pulse p3 having the frequency spectrum shown in FIG. 3 is transmitted from the ultrasonic probe 3. Then, as in the case of transmission of the ultrasonic pulses p1 and p2, a bubble echo Eb3 having a frequency spectrum, shown in FIG. 4, corresponding to that of the ultrasonic pulse p3 is obtained as a nonlinear component in a broad frequency band including the fundamental band. It is also considered that a tissue echo Ec3, which is a clutter component obtained from a tissue of a living body, in the reception echo E3 obtained by transmitting the ultrasonic pulse p3 is a substantially linear component in the fundamental band, as in the case of the tissue echoes Ec1 and Ec2, i.e., the clutter components of the reception echoes E1 and E2, respectively.

As described above, three kinds of ultrasonic pulses p1, p2, and p3, i.e., two ultrasonic pulses p1 and p2 having different frequency spectra and the ultrasonic pulse p3 obtained by adding these two ultrasonic pulses p1 and p2, are sequentially transmitted from the ultrasonic probe 3. Then, the reception echoes E1, E2, and E3 corresponding to the ultrasonic pulses p1, p2, and p3, respectively, are obtained and temporarily stored in the signal processing unit 7. In addition, in the fundamental band, the reception echoes E1, E2, and E3 contain the bubble echoes Eb1, Eb2, and Eb3, i.e., the nonlinear components, and the tissue echoes Ec1, Ec2, and Ec3, i.e., the substantially linear components, respectively. In addition, in convenience of explanation, an order of transmission is considered to be order of the ultrasonic pulses p1, p2 and p3. However, the order of transmission is not limited in order of the ultrasonic pulses p1, p2 and p3.

Then, at step S3, the signal processing unit 7 performs a linear operation on the reception echoes E1, E2, and E3. More specifically, the signal processing unit 7 adds the reception echoes E1 and E2, and then subtracts the reception echo E3. As described above, the reception echoes E1, E2, and E3 contain the bubble echoes Eb1, Eb2, and Eb3 and the tissue echoes Ec1, Ec2, and Ec3 as shown by Equations (1-1), (1-2), and (1-3), respectively.

[Equation 1]

$$E1 = Ec1 + Eb1 \quad (1\text{-}1)$$

$$E2 = Ec2 + Eb2 \quad (1\text{-}2)$$

$$E3 = Ec3 + Eb3 \quad (1\text{-}3)$$

In addition, the tissue echo Ec3 corresponds to the ultrasonic pulse p3 obtained by adding two ultrasonic pulses p1 and p2 corresponding to the tissue echoes Ec1 and Ec2, respectively. Each of the tissue echoes Ec1, Ec2, and Ec3 can be considered to be a substantially linear component. Thus, Equation (2) is derived.

[Equation 2]

$$Ec3 = Ec1 + Ec2 \quad (2)$$

On the other hand, since each of the bubble echoes Eb1, Eb2, and Eb3 is a nonlinear component, Equation (3) is derived.

[Equation 3]

$$Eb3 \neq Eb1 + Eb2 \quad (3)$$

Equation (4) is derived by adding the reception echoes E1 and E2, and subtracting the reception echo E3, using Equations (1-1), (1-2), (1-3), (2), and (3).

[Equation 4]

$$E1 + E2 - E3 = Ec1 + Eb1 + Ec2 + Eb2 - Ec3 - Eb3 = Eb1 + Eb2 - Eb3 = Eb \quad (4)$$

Accordingly, a result obtained by adding the reception echoes E1 and E2 and subtracting the reception echo E3 corresponds to a pulse signal Eb containing only components of the bubble echoes, which are nonlinear components in the fundamental band of each of the reception echoes E1, E2, and E3. That is, by performing the linear operation, it is possible to remove the tissue echoes Ec1, Ec2, and Ec3, which can be considered to be constituted by only substantially linear components in the fundamental band, from the reception echoes E1, E2, and E3, respectively.

On the other hand, generally, signal strengths of the bubble echoes Eb1, Eb2, and Eb3 are stronger than those of the tissue echoes Ec1, Ec2, and Ec3, respectively, in the fundamental band. In addition, since many nonlinear responses for the ultrasonic waves from the bubbles exist in the fundamental band, the bubble echoes, which are nonlinear components from the bubbles, remain as the pulse signal Eb by the linear operation.

The signal processing unit 7 then supplies the pulse signal Eb obtained by performing such signal processing to the detection unit 8.

Figure 5:
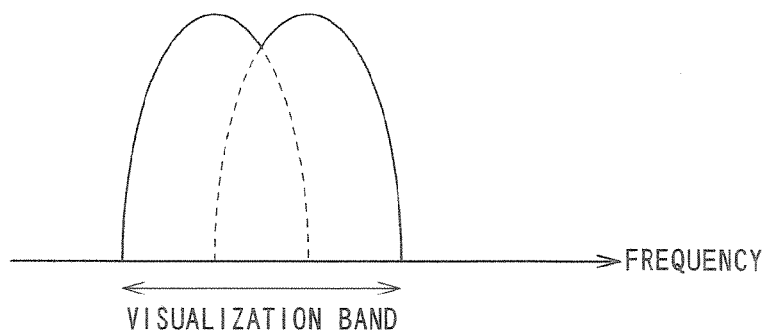
FIG. 5 is a diagram showing a visualization band visualized by the ultrasonic diagnostic apparatus shown in FIG. 1.

Next, at step S4, the fundamental band of the pulse signal Eb is selected as a visualization band, and components included therein are visualized. The visualization band of the pulse signal Eb is shown in FIG. 5. To perform visualization, the detection unit 8 performs envelope detection of the pulse signal Eb, and supplies the detection result to the display unit 11 as the detection signal. The display unit 11 then generates the video signal used for displaying images on the monitor from the detection signal received from the detection unit 8. The display unit 11 supplies the generated video signal to the monitor 4 to cause the monitor to display the image thereon.

As a result, a contrast image of the blood vessel of the object, obtained using the contrast medium, is displayed on the monitor 4. Since the contrast image is generated from the nonlinear components remaining at the fundamental band by the linear operation, the echoes reflected from the tissue are suppressed and the echoes reflected from the bubbles are selectively used for the visualization. In addition, since the echoes reflected from the bubbles having different radiuses are used for the visualization, the blood vessel is visualized more clearly in the contrast image.

It may be difficult to set or maintain the tomographic image to be clear in such a tissue-echo-suppressed contrast image.

Accordingly, at step S5, not only the contrast image but also the tissue image are generated and displayed. The reception echoes used for the generation of the contrast image and not having undergone the linear addition can be used for generation of the tissue image.

Figure 6:
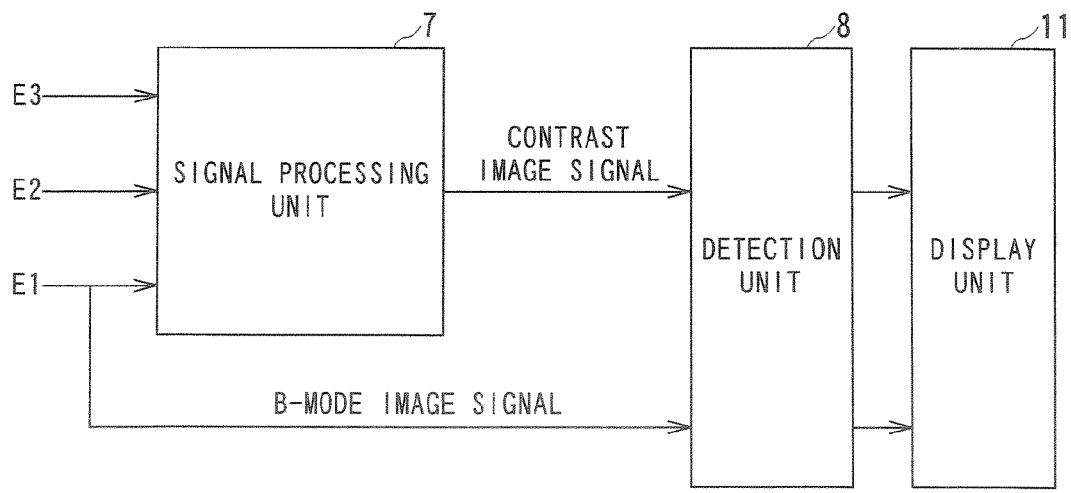
FIG. 6 is a block diagram showing a flow of a signal of reception echoes used as contrast image data and of the reception echoes used as background tissue image data by the ultrasonic diagnostic apparatus shown in FIG. 1.

FIG. 6 is a block diagram showing a flow of a signal of the reception echoes used as the contrast image data and of the reception echoes used as the background tissue image data by the ultrasonic diagnostic apparatus 1 shown in FIG. 1.

As shown in FIG. 6, after being fed to the signal processing unit 7 and having undergone the linear addition, the reception echoes E1, E2, and E3 are output to the detection unit 8 as a contrast image signal. Then, the detection signal generated from the contrast image pulse signal is supplied to the display unit 11, and the contrast image is displayed on the monitor 4.

Here, a given reception echo, e.g., the reception echo E1, not having undergone the linear addition by the signal processing unit 7 is obtained by the detection unit 8 as the tissue (B-mode) image signal. The detection unit 8 then detects the tissue echo components contained in the reception echo E1, and supplies the detection result to the display unit 11 as the detection signal for the tissue image. Furthermore, the display unit 11 generates a video signal of the tissue image used for displaying an image on the monitor from the detection signal, and supplies the generated video signal to the monitor 4, whereby the tissue image is displayed.

That is, by treating the reception echoes at the signal processing unit 7, the detection unit 8, and display unit 11 in parallel, it is possible to generate and display the tissue image as well as the contrast image. The contrast image and the tissue image generated in this manner can be displayed on the monitor 4 using an arbitrary display method.

Figure 7:
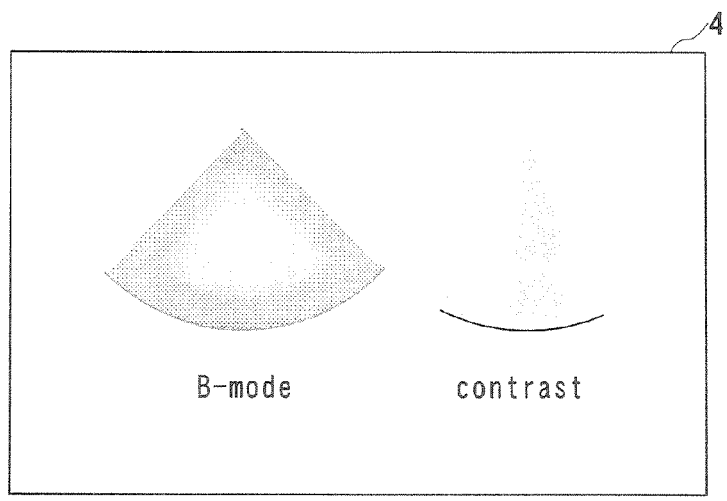
FIG. 7 is a schematic diagram showing an example of displaying a contrast image and a background tissue image in parallel on a monitor in the ultrasonic diagnostic apparatus shown in FIG. 1.
Figure 8:
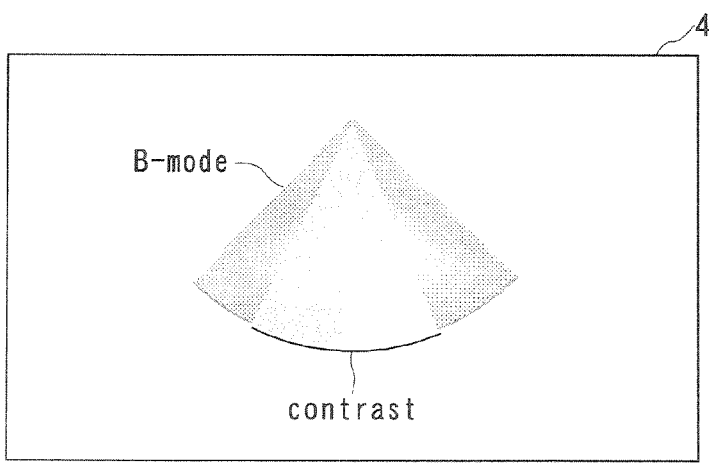
FIG. 8 is a schematic diagram showing an example of displaying the contrast image over the background tissue image on the monitor in the ultrasonic diagnostic apparatus shown in FIG. 1.

FIG. 7 is a schematic diagram showing an example of displaying the contrast image and the background tissue image in parallel (hereinafter, referred to as "parallel display") on the monitor 4 in the ultrasonic diagnostic apparatus 1 shown in FIG. 1. In addition, FIG. 8 is a schematic diagram showing an example of displaying the contrast image over the background tissue image (hereinafter, referred to as "superimposed display") on the monitor 4 in the ultrasonic diagnostic apparatus 1 shown in FIG. 1. Furthermore, FIG. 9 is a schematic diagram showing an example of displaying the contrast image and the background tissue image on the monitor 4 so that the background tissue image is seen through the contrast image (hereinafter, referred to as "see-through display") in the ultrasonic diagnostic apparatus 1 shown in FIG. 1.

Figure 9:
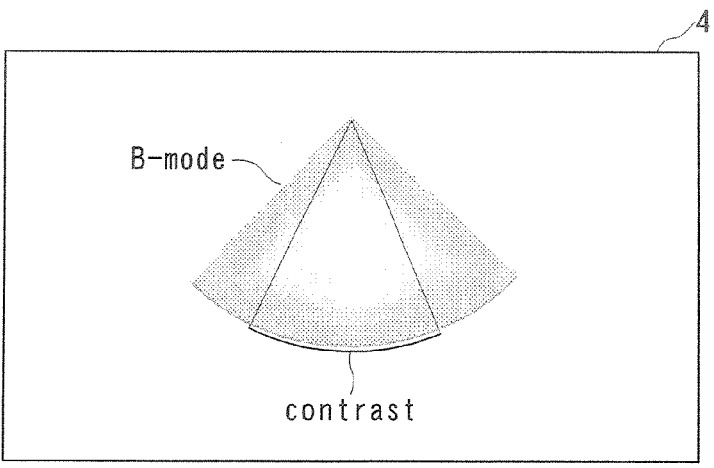
FIG. 9 is a schematic diagram showing an example of displaying the contrast image and the background tissue image on the monitor so that the background tissue image is seen through the contrast image in the ultrasonic diagnostic apparatus shown in FIG. 1.

In addition to the parallel display, the superimposed display, and the see-through display of the contrast image and the tissue image as shown in FIGS. 7, 8, and 9, it may be also possible to switch the display screen to display the contrast image and the tissue image (hereinafter, referred to as "switching display").

The ultrasonic diagnostic apparatus 1 having the above-described configuration transmits a plurality of ultrasonic pulses having different frequency distributions (frequency spectra) and an ultrasonic pulse obtained by linearly adding each of the ultrasonic pulses. The ultrasonic diagnostic apparatus 1 then calculates the difference between the result of the addition of the reception echoes corresponding to the former ultrasonic pulses and the reception echo corresponding to the latter ultrasonic pulse. The ultrasonic diagnostic apparatus 1 visualizes the components in the fundamental band of the difference.

Accordingly, it is possible to sufficiently suppress the echoes from the tissue and to visualize the echoes from bubbles that response the different frequencies, i.e., the bubbles having different radiuses. This can improve the sensitivity of the ultrasonic diagnostic apparatus 1.

An example of transmitting two ultrasonic pulses having different center frequencies has been shown. However, after N ultrasonic pulses having different center frequencies and an ultrasonic pulse obtained by combining N ultrasonic pulses are transmitted in the same manner, the linear addition may be performed on each reception echo.

An alternative example of a combination of a frequency spectrum of each ultrasonic pulse to be transmitted by the ultrasonic diagnostic apparatus 1 will be described next.

Figure 10:
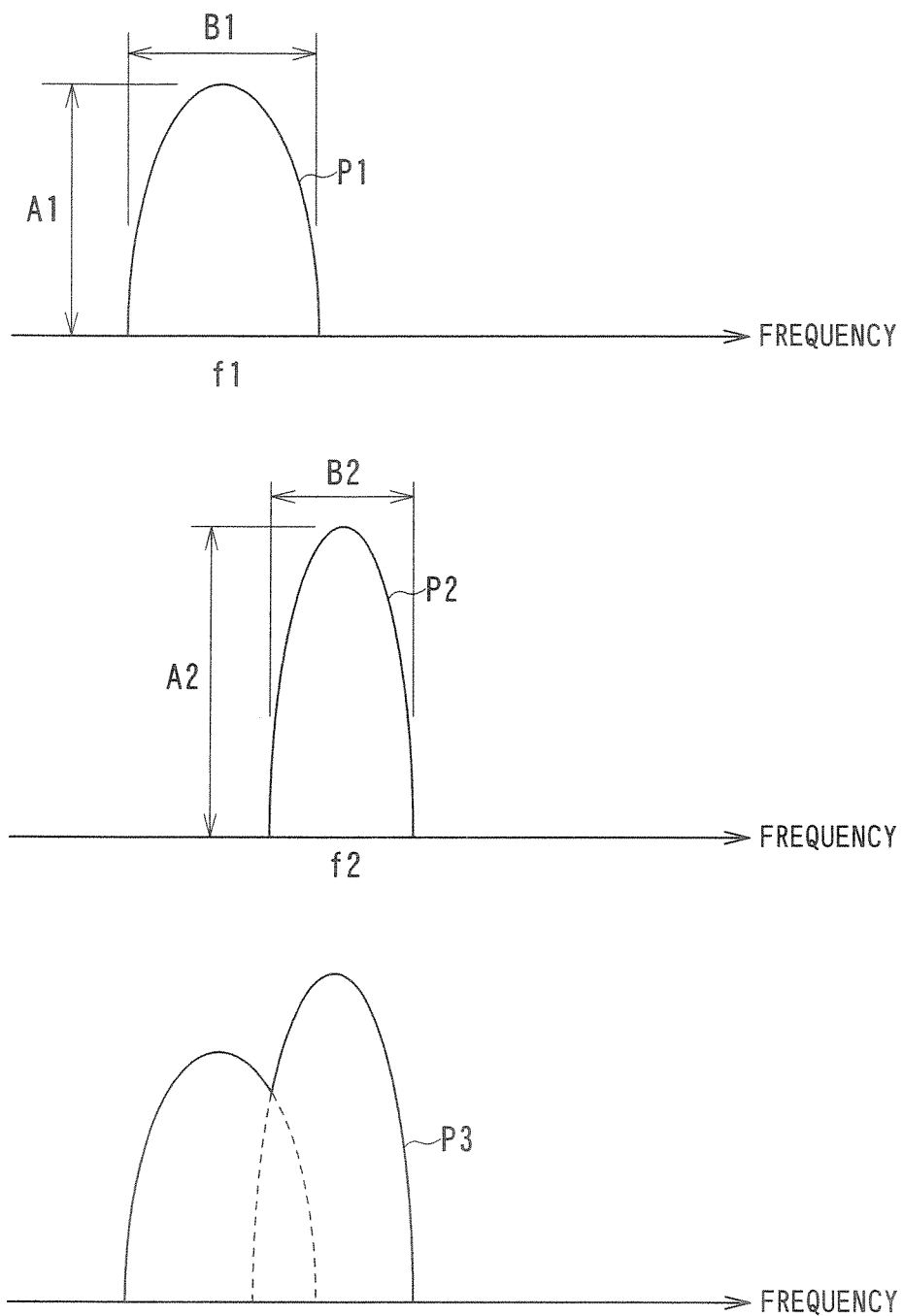
FIG. 10 is a diagram showing an alternative example of a combination of a frequency spectrum of each ultrasonic pulse to be transmitted by the ultrasonic diagnostic apparatus shown in FIG. 1.

FIG. 10 is a diagram showing an alternative example of a combination of a frequency spectrum of each ultrasonic pulse to be transmitted by the ultrasonic diagnostic apparatus 1 shown in FIG. 1.

As shown in FIG. 10, the ultrasonic pulses p1, p2 and p3 can be set to have various frequency spectra. Regarding the ultrasonic pulses p1 and p2, at least one of the center frequency, the amplitude, and the band can be set to differ from one another. In addition, the ultrasonic pulses p1 and p2 can be sequentially transmitted toward the microbubbles in the object from the ultrasonic probe 3 with at least one of a phase and a transmission focus being differed. In the example shown in FIG. 10, the ultrasonic pulse p1 having a frequency spectrum centered at the center frequency f1, whose amplitude and band are set at A1 and B1, is transmitted from the ultrasonic probe 3 at a phase C1 and a transmission focus F1. On the other hand, the ultrasonic pulse p2 having a frequency spectrum centered at the center frequency f2, whose amplitude and band are set at A2 and B2, is transmitted from the ultrasonic probe 3 at a phase C2 and a transmission focus F2.

In addition, the ultrasonic pulse p3 is obtained by combining the ultrasonic pulses p1 and p2. More specifically, the ultrasonic pulse p3 corresponds to a signal obtained by linearly addition the ultrasonic pulses p1 and p2, and multiplying the amplitude by A, and shifting the phase by "$\Delta C(C2-C1)$".

The signal processing unit 7 then obtains the reception echoes E1, E2, and E3 obtained by transmitting such ultrasonic pulses p1, p2, and p3.

The signal processing unit 7 performs phase correction to shift the phase of the reception echo E3 obtained by transmitting the ultrasonic pulse p3 by "$-\Delta C$" and amplitude correction to multiply the amplitude by 1/A. As shown by Equation (5), a reception echo E3' having undergone the phase correction and the amplitude correction is subtracted from a result of adding the reception echoes E1 and E2 obtained by transmitting the ultrasonic pulses p1 and p2, respectively, whereby the pulse signal Eb containing components of the bubble echoes is generated.

[Equation 5]

$$Eb = E1 + E2 - E3' \quad (5)$$

As described above, a plurality of ultrasonic pulses having given frequency spectra different from one another and a combined ultrasonic pulse obtained by performing the linear operation on at least some of these ultrasonic pulses may be transmitted.

That is, the amplitude and the phase of the ultrasonic pulses to be transmitted can be set at any values if necessary. In addition, the amplitude correction and/or the phase correction can be performed on the reception echoes according to the amplitude and the phase of the transmitted ultrasonic pulses. Thus, it becomes possible to generate ultrasonographic images matching imaging conditions and purposes.

For example, it may be possible to sufficiently reduce the amplitude of the ultrasonic pulse to be transmitted so as not to destroy the bubbles injected into the object as the contrast medium. At the same time, it may be possible to perform the amplitude correction to increase the amplitude of the reception echoes. In addition, it may be possible to set the ultrasonic pulse p3 as −(ultrasonic pulses p1+p2) by inverting the phases of the ultrasonic pulses to be transmitted to obtain the target reception echoes. In such a case, the processing for generating the pulse signal Eb is represented by Equation (6), and the signal components from the tissue are suppressed and the signal components from the bubbles remain.

[Equation 6]

$$Eb = E1 + E2 + E3 \quad (6)$$

According to the ultrasonic diagnostic apparatus 1 and the ultrasonic diagnostic method according to the embodiment, the ultrasonic echoes reflected from the tissue of the living body are suppressed and the ultrasonic echoes reflected from more bubbles having different radiuses are visualized, thereby allowing easy recognition of the contrast enhancement by the bubbles at a higher sensitivity.

Figure 11:
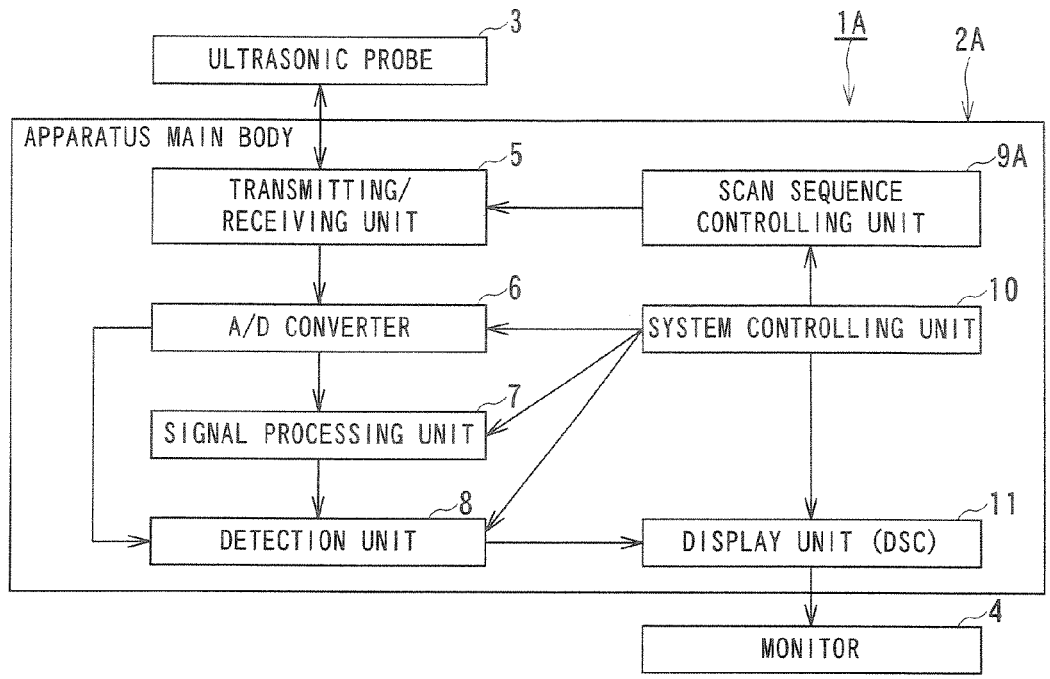
FIG. 11 is a diagram showing a configuration of an ultrasonic diagnostic apparatus according to a second embodiment of the present invention.

FIG. 11 is a diagram showing a configuration of an ultrasonic diagnostic apparatus according to a second embodiment of the present invention.

An ultrasonic diagnostic apparatus 1A according to the second embodiment is constituted by an apparatus main body 2A, an ultrasonic probe 3, and a monitor 4. The apparatus main body 2A has a transmitting/receiving unit 5, an A/D converter 6, a signal processing unit 7, a detection unit 8, a scan sequence controlling unit 9A, a system controlling unit 10, and a display unit 11. Each unit in the apparatus main body 2A may be implemented by circuits or by a CPU of a computer loading a control program. The same units in the ultrasonic diagnostic apparatus 1A shown in FIG. 11 as those in the ultrasonic diagnostic apparatus 1 shown in FIG. 1 are denoted by the same numerals, and description thereof is omitted.

The scan sequence controlling unit 9A not only performs the function of the scan sequence controlling unit 9 but also generates a scan sequence signal so that ultrasonic pulses p1 and p4 whose frequency bands do not overlap each other are transmitted from the ultrasonic probe 3 at regular intervals. It is preferable that the ultrasonic pulses p1 and p4 have relatively narrow frequency bands.

An operation of the ultrasonic diagnostic apparatus 1A will be described next.

Figure 12:
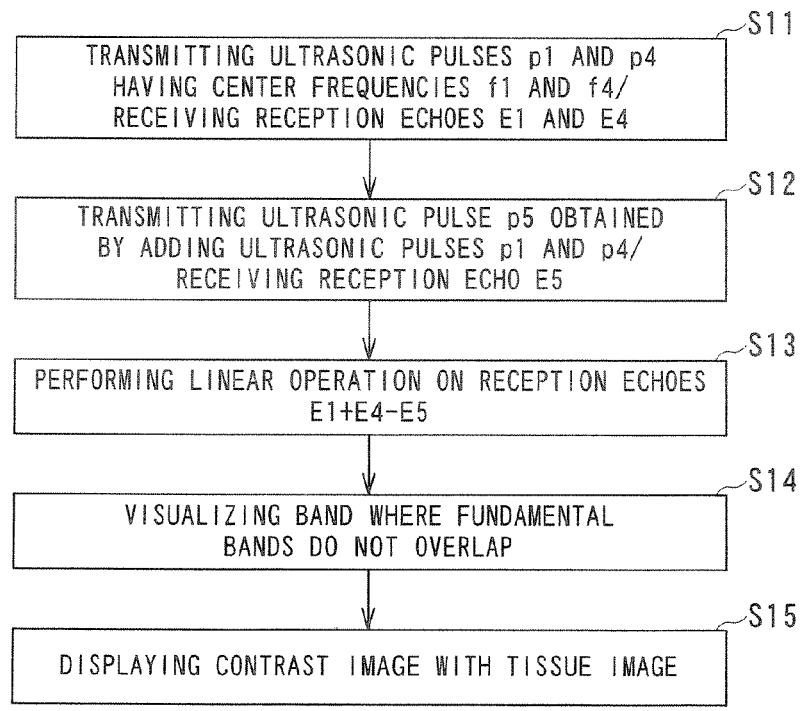
FIG. 12 is a flowchart showing a procedure that the ultrasonic diagnostic apparatus shown in FIG. 11 performs when visualizing a blood flow according to a contrast echo method using microbubbles as a contrast medium.

FIG. 12 is a flowchart showing a procedure that the ultrasonic diagnostic apparatus 1A shown in FIG. 11 performs when visualizing the blood flow according to the contrast echo method using microbubbles as a contrast medium. An alphabet "S" followed by a numeral in the figure represents each step of the flowchart.

Steps S11 to S13 and step S15 correspond to steps S1 to S3 and step S5 described using FIG. 2, if the ultrasonic pulses p2 and p3 are replaced by the ultrasonic pulses p4 and p5, respectively. In addition, in convenience of explanation, an order of transmission is considered to be order of the ultrasonic pulses p1, p4 and p5. However, the order of transmission is not limited in order of the ultrasonic pulses p1, p4 and p5.

Figure 13:
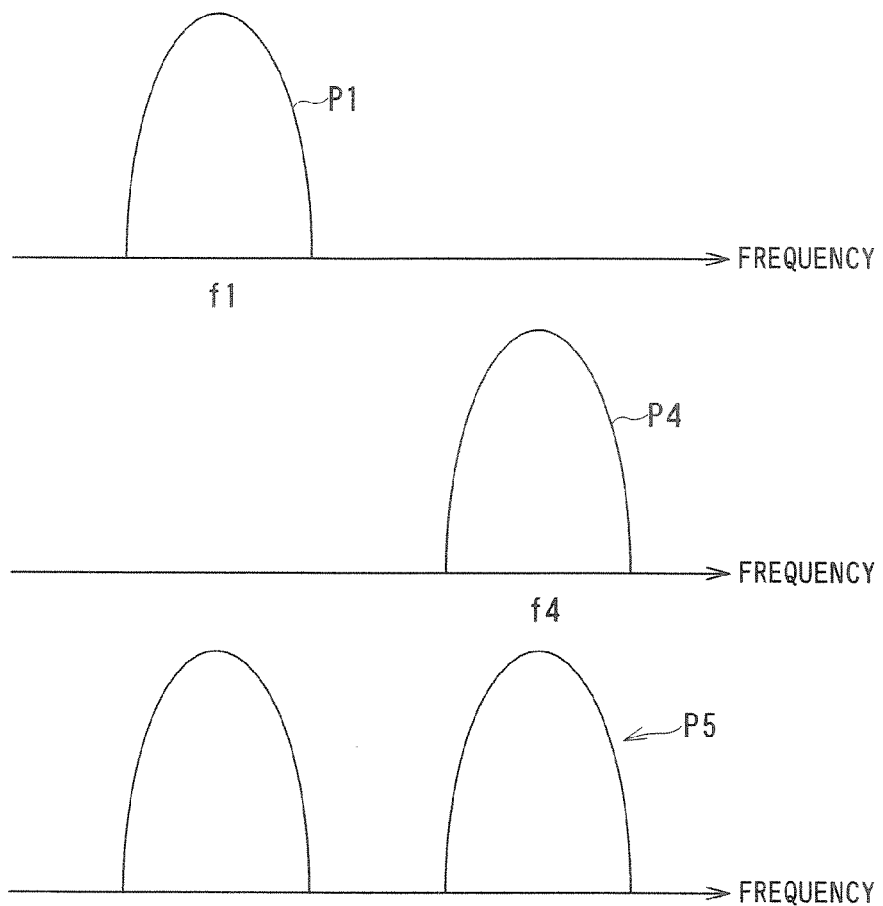
FIG. 13 is a schematic diagram showing an example of frequency spectra for a plurality of ultrasonic pulses to be sequentially transmitted from an ultrasonic probe of the ultrasonic diagnostic apparatus shown in FIG. 11.

FIG. 13 is a schematic diagram showing an example of frequency spectra for the ultrasonic pulses p1, p4, and p5 sequentially transmitted from the ultrasonic probe 3 at steps S11 and S12. Each frequency spectrum shown in FIG. 13 is an alternative example of the corresponding frequency spectrum shown in FIGS. 3 and 10.

Horizontal axes of FIG. 13 represent the frequency. FIG. 13 shows the ultrasonic pulse p1 having an ultrasonic spectrum centered at the center frequency f1, the ultrasonic pulse p4 having an ultrasonic spectrum centered at the center frequency f4, and the ultrasonic pulse p5 obtained by adding the ultrasonic pulses p1 and p4.

Figure 14:
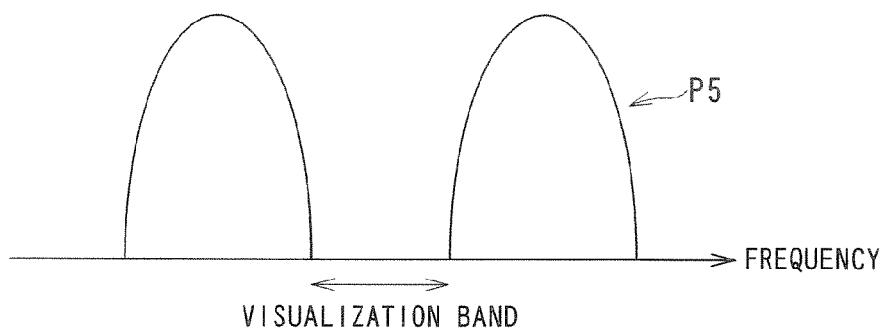
FIG. 14 is a diagram showing a visualization band visualized by the ultrasonic diagnostic apparatus shown in FIG. 11.

At step S14, a band of a pulse signal Eb including no overlapped fundamental bands is selected as a visualization band, and components included therein are visualized. The visualization band of the pulse signal Eb is shown in FIG. 14. The display unit 11 then generates a video signal used for displaying images on the monitor from a detection signal received from the detection unit 8. The display unit 11 supplies the generated video signal to the monitor 4 to cause the monitor to display the image thereon.

For example, when visualizing a moving organ such as a heart, an effect of the movement causes a change at each part of reception signals having a rate. As a result, the fundamental wave remains, which causes a motion artifact on the ultrasonographic image. Accordingly, the ultrasonic diagnostic apparatus 1A according to the embodiment reduces tissue echoes by visualizing components in a band where the fundamental bands do not overlap, namely an area where there are not tissue echoes, at step S14, which can reduce the motion artifact on the ultrasonographic image.

In addition, an echo having a center frequency f1 corresponding to the ultrasonic pulse p1 contains nonlinear components and includes harmonic components each having a frequency equal to an integral multiple of the frequency f1. Thus, preferably, the center frequency f4 of the ultrasonic pulse p4 is set at an integral multiple (double or more) of the center frequency f1 of the ultrasonic pulse p1, and a band where the fundamental bands do not overlap is selected as the visualization band and components included therein is visualized.

According to the ultrasonic diagnostic apparatus 1A and the ultrasonic diagnostic method according to the embodiment, the ultrasonic echoes reflected from the tissue of the living body are suppressed and the ultrasonic echoes reflected from more bubbles having different radiuses are visualized, thereby allowing easy recognition of the contrast enhancement by the bubbles at a higher sensitivity.

In addition, according to the ultrasonic diagnostic apparatus 1A and the ultrasonic diagnostic method according to the embodiment, by setting the visualization band to exclude the fundamental components, the motion artifact of the ultrasonographic image can be reduced.

Figure 15:
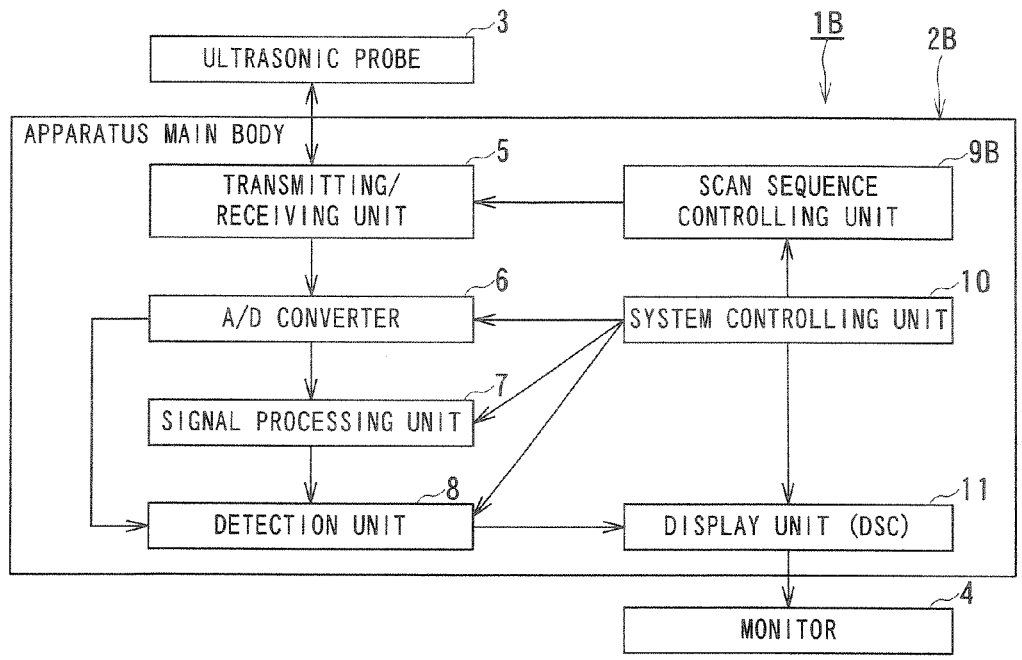
FIG. 15 is a diagram showing a configuration of an ultrasonic diagnostic apparatus according to a third embodiment of the present invention.

FIG. 15 is a diagram showing a configuration of an ultrasonic diagnostic apparatus according to a third embodiment of the present invention.

An ultrasonic diagnostic apparatus 1B according to the third embodiment is constituted by an apparatus main body 2B, an ultrasonic probe 3, and a monitor 4. The apparatus main body 2B has a transmitting/receiving unit 5, an A/D converter 6, a signal processing unit 7, a detection unit 8, a scan sequence controlling unit 9B, a system controlling unit 10, and a display unit 11. Each unit in the apparatus main body 2B may be implemented by circuits or by a CPU of a computer loading a control program. The same units in the ultrasonic diagnostic apparatus 1B shown in FIG. 15 as those in the ultrasonic diagnostic apparatus 1 shown in FIG. 1 are denoted by the same numerals, and description thereof is omitted.

The scan sequence controlling unit 9B not only performs the function of the scan sequence controlling unit 9 but also generates a scan sequence signal so that ultrasonic pulses p1 and p2 having different frequency spectra are transmitted from the ultrasonic probe 3 at regular intervals with a phase of one of the pulses being inverted. In addition, as for the ultrasonic diagnostic apparatus 1B, a combination with the ultrasonic diagnostic apparatus 1A is possible.

An operation of the ultrasonic diagnostic apparatus 1B will be described next.

Figure 16:
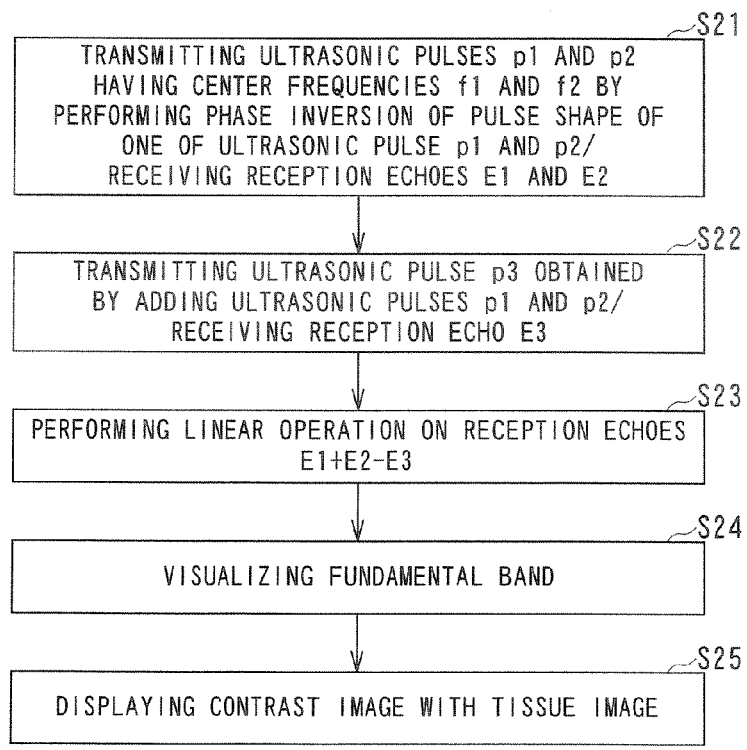
FIG. 16 is a flowchart showing a procedure that the ultrasonic diagnostic apparatus shown in FIG. 15 performs when visualizing a blood flow according to a contrast echo method using microbubbles as a contrast medium.

FIG. 16 is a flowchart showing a procedure that the ultrasonic diagnostic apparatus 1B shown in FIG. 15 performs when visualizing the blood flow according to the contrast echo method using microbubbles as a contrast medium. An alphabet "S" followed by a numeral in the figure represents each step of the flowchart.

At step S21, the ultrasonic diagnostic apparatus 1B performs phase inversion of a pulse shape of one of the ultrasonic pulse p1 having the center frequency f1 and the ultrasonic pulse p2 having the center frequency f2, and transmits the ultrasonic pulses. The ultrasonic diagnostic apparatus 1B then receives the reception echoes E1 and E2.

Steps S22 to S25 correspond to steps S2 and S5 described using FIG. 2, respectively. In addition, in convenience of explanation, an order of transmission is considered to be order of the ultrasonic pulses p1, p2 and p3. However, the order of transmission is not limited in order of the ultrasonic pulses p1, p2 and p3.

Figure 17:
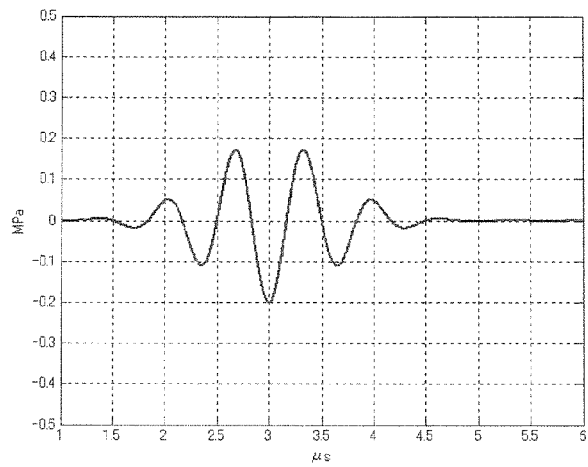
FIG. 17 is a diagram showing an example of two pulse shapes of ultrasonic pulses when two ultrasonic pulses having different frequency spectra are transmitted in phase, and of a pulse shape obtained by combining these pulse shapes.
Figure 17:
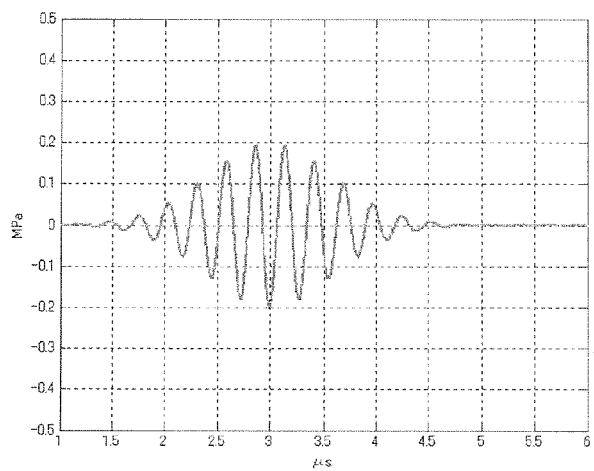
Figure 17:
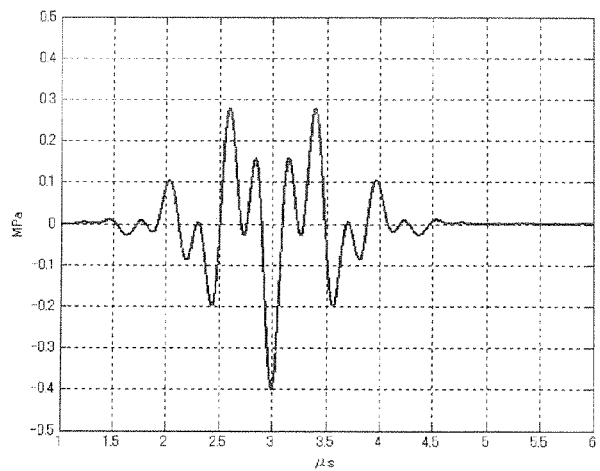
Figure 18:
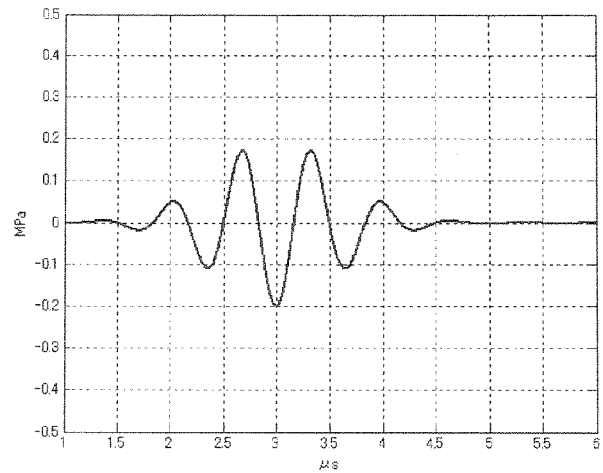
FIG. 18 is a diagram showing an example of two pulse shapes of ultrasonic pulses when two ultrasonic pulses having different center frequencies are transmitted with a phase of one of the ultrasonic pulses being inverted, and of a pulse shape obtained by combining these pulse shapes.
Figure 18:
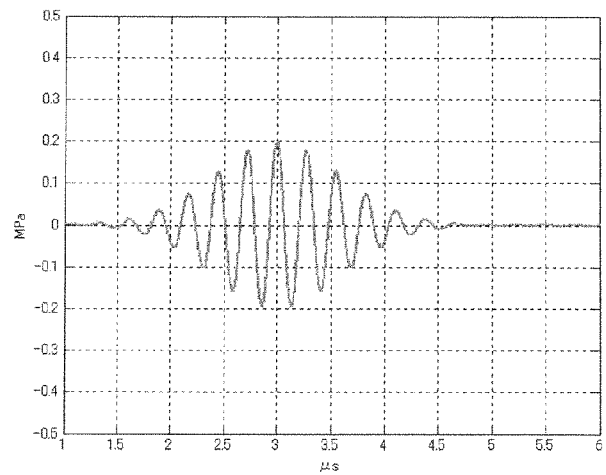
Figure 18:
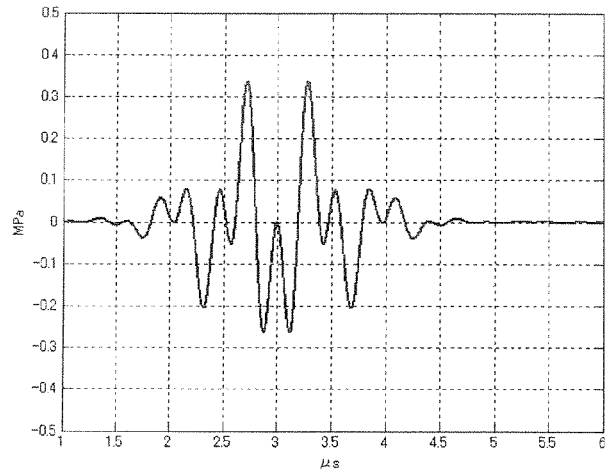

FIG. 17 is a diagram showing an example of two pulse shapes of the ultrasonic pulses when two ultrasonic pulses having different frequency spectra (in FIGS. 17 and 18, different center frequencies) are transmitted in phase, and of a pulse shape obtained by combining these pulse shapes. On the other hand, FIG. 18 shows shapes of three pulses transmitted by the ultrasonic diagnostic apparatus 1B. More specifically, FIG. 18 is a diagram showing an example of two pulse shapes of the ultrasonic pulses when two ultrasonic pulses having different center frequencies are transmitted with the phase of one of the ultrasonic pulses being inverted, and of a pulse shape obtained by combining these pulse shapes.

Horizontal axes shown in FIGS. 17 and 18 represent time. Three pulse shapes shown in FIG. 17 correspond to pulse shapes of the ultrasonic pulses p1 and p2 when the ultrasonic pulses p1 and p2 having different center frequencies are transmitted in phase, and a pulse shape obtained by combining the pulse shapes of the ultrasonic pulses p1 and p2 when the pulses are transmitted in phase.

On the other hand, three pulse shapes shown in FIG. 18 correspond to pulse shapes of the ultrasonic pulses p1 and p2 when the ultrasonic pulses p1 and p2 having different center frequencies are transmitted with the phase of one of the pulses (e.g., the ultrasonic pulse p2) being inverted, and a pulse shape of an ultrasonic pulse p3 obtained by combining the ultrasonic pulses p1 and p2 having opposite phases by the linear operation. Compared with the pulse shape of the ultrasonic pulse p3 shown in FIG. 17, the peak is reduced in the pulse shape of the ultrasonic pulse p3 shown in FIG. 18. When the peak in the pulse shape of the ultrasonic pulse p3 decreases as shown in FIG. 18, the saturation of the received echo signals caused by the transmission of the ultrasonic pulse p3 is advantageously reduced. That is, when the peak in the pulse shape of the ultrasonic pulse p3 decreases as shown in FIG. 18, the gain of the received echo signals caused by the transmission of the ultrasonic pulse p3 is advantageously set at a greater value.

Figure 19:
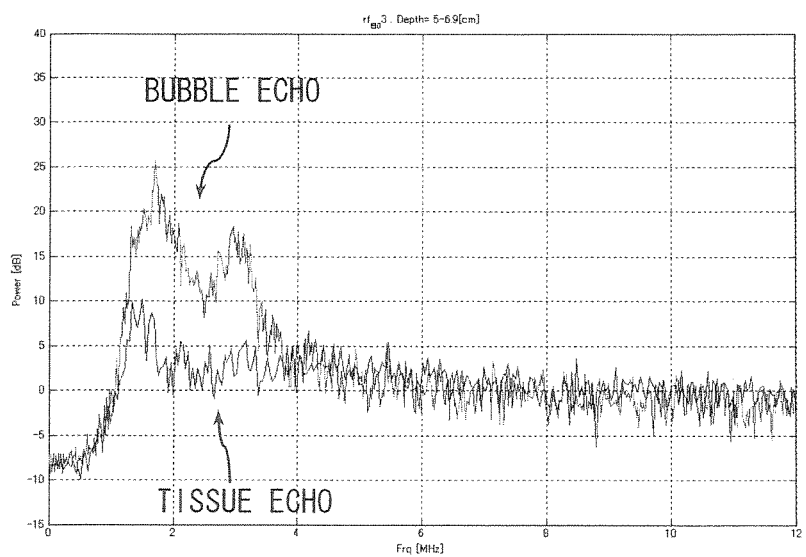
FIG. 19 is a diagram showing frequency spectra of a bubble echo and a tissue echo when the one of the ultrasonic pulses is inverted and is not inverted.
Figure 19:
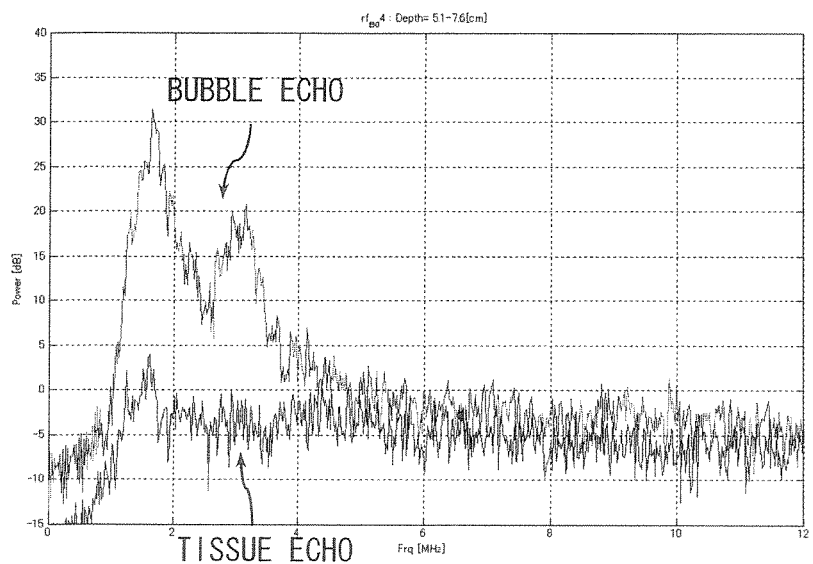

FIG. 19 is a diagram showing frequency spectra of the bubble echo and the tissue echo when the one of the ultrasonic pulses is inverted and is not inverted.

The upper diagram of FIG. 19 shows the frequency spectra of the bubble echo and the tissue echo when the ultrasonic pulses p1, p2, and p3 having the pulse shapes shown in FIG. 17 are transmitted. On the other hand, the lower diagram of FIG. 19 shows the frequency spectra of the bubble echo and the tissue echo when the ultrasonic pulses p1, p2, and p3 having the pulse shapes shown in FIG. 18 are transmitted.

FIG. 19 shows that, when the ultrasonic pulses having the pulse shapes shown in FIG. 18 are transmitted, the saturation of the echo signal is reduced, which allows an increase in the signal strength of the bubble echo and a decrease in the signal strength of the tissue echo. When the saturation of the echo signal is caused, it cannot cancel the clutter components for the linear operation by the tissue echo becoming $Ec1 \neq Ec2 \neq Ec3$.

According to the ultrasonic diagnostic apparatus 1B and the ultrasonic diagnostic method according to the embodiment, the ultrasonic echoes reflected from the tissue of the living body are suppressed and the ultrasonic echoes reflected from more bubbles having different radiuses are visualized, thereby allowing easy recognition of the contrast enhancement by the bubbles at a higher sensitivity.

In addition, according to the ultrasonic diagnostic apparatus 1B and the ultrasonic diagnostic method according to the embodiment, by performing the phase inversion of the ultrasonic pulse p2 so as to reduce the peaks in the pulse shape of the ultrasonic pulse p3, the signal strength of the bubble echo can be increased, whereas the signal strength of the tissue echo can be reduced.

Figure 20:
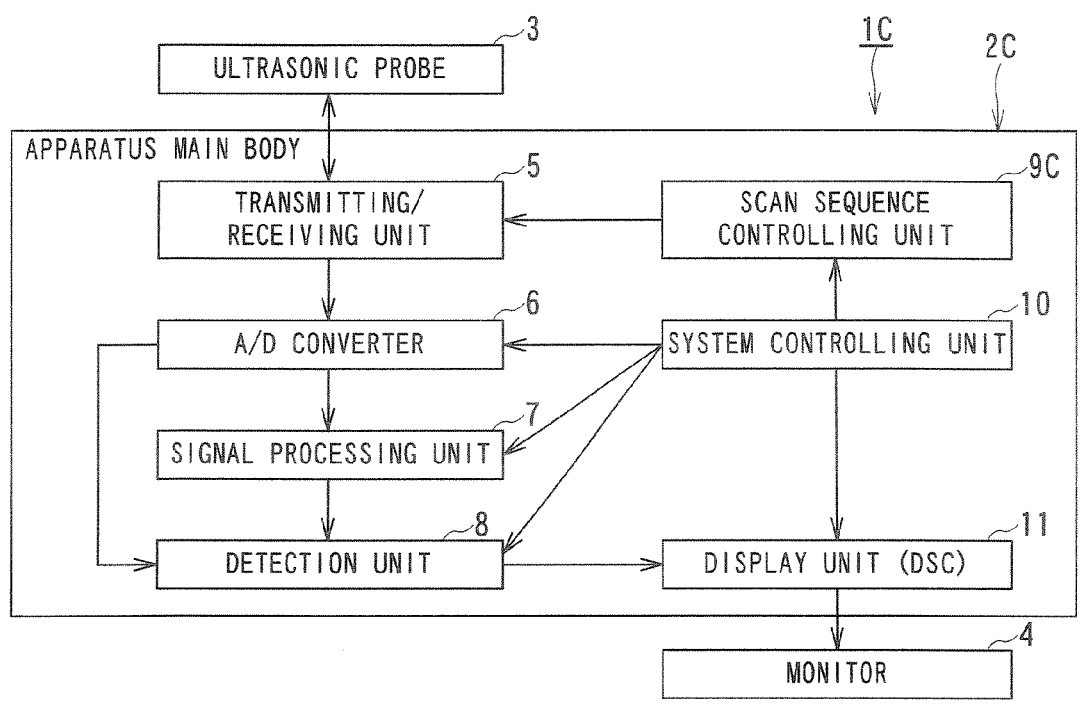
FIG. 20 is a diagram showing a configuration of an ultrasonic diagnostic apparatus according to a fourth embodiment of the present invention.

FIG. 20 is a diagram showing a configuration of an ultrasonic diagnostic apparatus according to a fourth embodiment of the present invention.

An ultrasonic diagnostic apparatus 1C according to the fourth embodiment is constituted by an apparatus main body 2C, an ultrasonic probe 3, and a monitor 4. The apparatus main body 1C has a transmitting/receiving unit 5, an A/D converter 6, a signal processing unit 7, a detection unit 8, a scan sequence controlling unit 9C, a system controlling unit 10, and a display unit 11. Each unit in the apparatus main body 2C may be implemented by circuits or by a CPU of a computer loading a control program. The same units in the ultrasonic diagnostic apparatus 1C shown in FIG. 20 as those in the ultrasonic diagnostic apparatus 1 shown in FIG. 1 are denoted by the same numerals, and description thereof is omitted.

Compared with the scan sequence controlling unit 9, the scan sequence controlling unit 9C employs different usage of the ultrasonic probe 3 and different ultrasonic pulses to be transmitted. In addition, as for the ultrasonic diagnostic apparatus 1C, a combination with at least one is possible among the ultrasonic diagnostic apparatus 1, 1A and 1B.

An operation of the ultrasonic diagnostic apparatus 1C is substantially the same as that of the ultrasonic diagnostic apparatus 1 shown in FIG. 1, the ultrasonic diagnostic apparatus 1A, or the ultrasonic diagnostic apparatus 1B except for the usage of the ultrasonic probe 3 and the ultrasonic pulses to be transmitted.

FIGS. 21 to 24 are diagrams illustrating a method for transmitting the ultrasonic pulses employed by the ultrasonic diagnostic apparatus 1C shown in FIG. 20.

As shown in FIGS. 21 to 24, in the ultrasonic diagnostic apparatus 1C, different transmission apertures 3a of the ultrasonic probe 3 used for the transmission/reception are used for each transmission/reception. That is, the transmission apertures 3a of the ultrasonic probe 3 are divided into a plurality of groups, each having at least one different ultrasonic transducer. Dividing the transmission apertures 3a of the ultrasonic probe 3 into a plurality of groups, each having at least one exclusive ultrasonic transducer, is easier for controlling and is practical.

Figure 21:
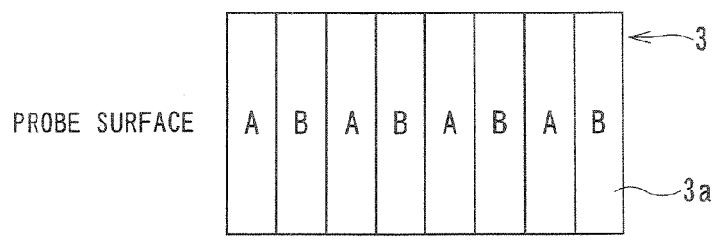
FIG. 21 is a diagram illustrating a method for transmitting an ultrasonic pulse employed by the ultrasonic diagnostic apparatus shown in FIG. 20.

For example, as shown in FIG. 21, when the ultrasonic probe 3 has a plurality of transmission apertures 3a arranged one-dimensionally on a probe surface, a first transmission aperture group A and a second transmission aperture group B are set. For example, the first transmission aperture group A and the second transmission aperture group B do not have a common part, and are exclusive.

Figure 22:
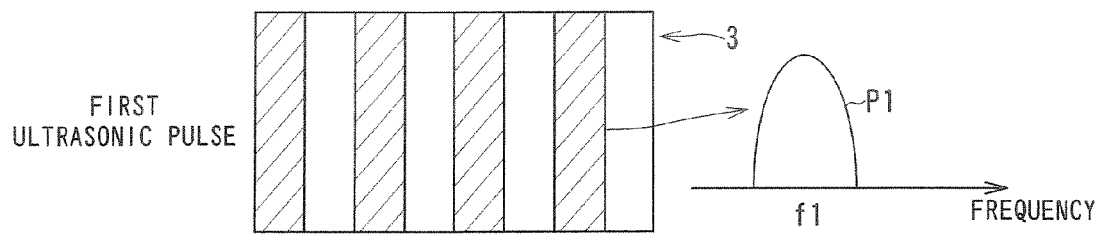
FIG. 22 is a diagram illustrating the method for transmitting the ultrasonic pulse employed by the ultrasonic diagnostic apparatus shown in FIG. 20.

As shown in shaded areas of FIG. 22, only the transmission apertures 3a belonging to the first transmission aperture group A is firstly used for the transmission. The first ultrasonic pulse p1 having the frequency spectrum centered at the center frequency f1 is transmitted from the transmission apertures 3a belonging to the first transmission aperture group A. Then, a first sound field is formed by the first ultrasonic pulse p1, and the reception echo E1 corresponding to the first sound field can be obtained.

Figure 23:
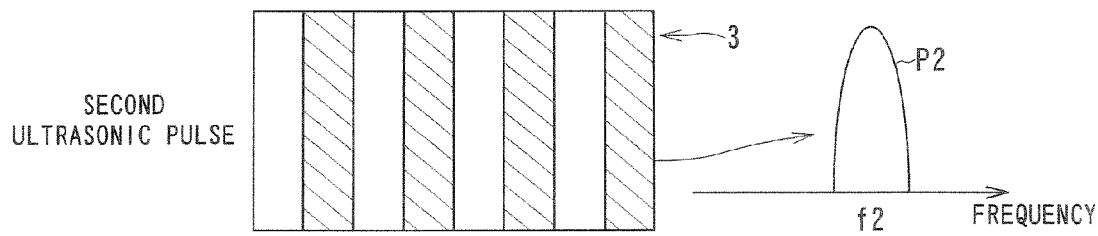
FIG. 23 is a diagram illustrating the method for transmitting the ultrasonic pulse employed by the ultrasonic diagnostic apparatus shown in FIG. 20.

Next, as shown in shaded areas of FIG. 23, only the transmission apertures 3a belonging to the second transmission aperture group B is then used for the transmission. The second ultrasonic pulse p2 having the frequency spectrum centered at the center frequency f2, which is different from the center frequency f1 of the first ultrasonic pulse p1, is transmitted from the transmission apertures 3a belonging to the second transmission aperture group B. Then, a second sound field is formed by the second ultrasonic pulse p2, and the reception echo E2 corresponding to the second sound field can be obtained. Here, parameters of the second ultrasonic pulse p2 other than the center frequency f2, such as the band B2 and the amplitude A2, may be set at values different from parameters, such as the band B1 and the amplitude A1, of the first ultrasonic pulse p1.

Figure 24:
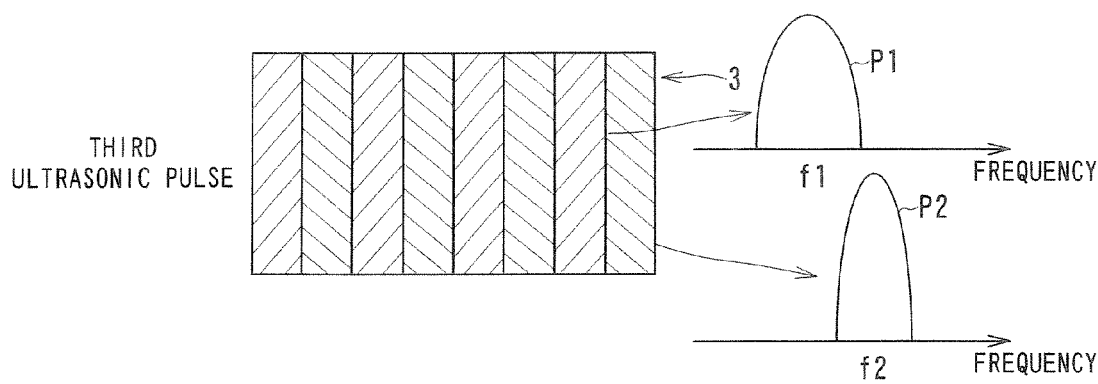
FIG. 24 is a diagram illustrating the method for transmitting the ultrasonic pulse employed by the ultrasonic diagnostic apparatus shown in FIG. 20.

Then, as shown in FIG. 24, both the transmission apertures 3a belonging to the first transmission aperture group A and the transmission apertures 3a belonging to the second transmission aperture group B are used for the transmission at the same time. The first ultrasonic pulse p1 having the frequency spectrum centered at the center frequency f1 is transmitted from the transmission apertures 3a belonging to the first transmission aperture group A, while the second ultrasonic pulse p2 having the frequency spectrum centered at the center frequency f2 is transmitted from the transmission apertures 3a belonging to the second transmission aperture group B. Then, a third sound field is formed by the first ultrasonic pulse p1 and the second ultrasonic pulse p2, and the reception echo E3 corresponding to the third sound field can be obtained.

The reception echo E3 obtained from the third sound field formed by simultaneously transmitting the first ultrasonic pulse p1 and the second ultrasonic pulse p2 is equivalent to a reception echo obtained when a third ultrasonic pulse p3, which is obtained by combining the first ultrasonic pulse p1 and the second ultrasonic pulse p2. That is, simultaneously transmitting the first ultrasonic pulse p1 and the second ultrasonic pulse p2 from the transmission apertures 3a, belonging to the different groups, of the ultrasonic probe 3 is substantially equivalent to transmitting the third ultrasonic pulse p3 obtained by combining the first ultrasonic pulse p1 and the second ultrasonic pulse p2.

The ultrasonic diagnostic apparatus 1C is configured to transmit the ultrasonic pulses p1 and p2, which have not been combined, from the different transmission apertures 3a so as to compose the ultrasonic pulse p3 to be combined not as a transmission pulse but as a transmission sound field. That is, the ultrasonic diagnostic apparatus 1C not only transmits the ultrasonic pulses p1 and p2, which have not been combined, by switching the channels to be used in the ultrasonic probe 3 but also composes the ultrasonic pulse p3 as the transmission sound field using both channels used for transmitting the ultrasonic pulses p1 and p2.

Accordingly, as in the case of the ultrasonic diagnostic device 1 shown in FIG. 1, the ultrasonic diagnostic device 1C can suppress the tissue echo and visualize the echoes reflected from the bubbles having different radiuses, thereby allowing improvement of the visualization sensitivity of the blood flow. Furthermore, since the ultrasonic pulse p3 is composed as the transmission sound field, the advantage from the suppression of the tissue echo can be sufficiently provided, even if a pulser included in the transmitting/receiving unit 5 does not have a sufficient capability of accurately generating and transmitting the ultrasonic pulse p3 to be combined.

A transmission order shown in FIGS. 22 to 24 may be changed randomly. In addition, the transmission apertures 3a may be divided into three or more transmission aperture groups, and three or more ultrasonic pulses having different frequency spectra may be composed as a sound field. Additionally, ultrasonic transducers common to each transmission aperture group may exist as long as the desired sound field can be formed. In addition, there may be an ultrasonic transducer that is not used.

Furthermore, the phase correction and the amplitude correction may be performed in the linear operation of the reception echo by the signal processing unit 7.

According to the ultrasonic diagnostic apparatus 1C and the ultrasonic diagnostic method according to the embodiment, the ultrasonic echoes reflected from the tissue of the living body are suppressed and the ultrasonic echoes reflected from more bubbles having different radiuses are visualized, thereby allowing easy recognition of the contrast enhancement by the bubbles at a higher sensitivity.

Figure 25:
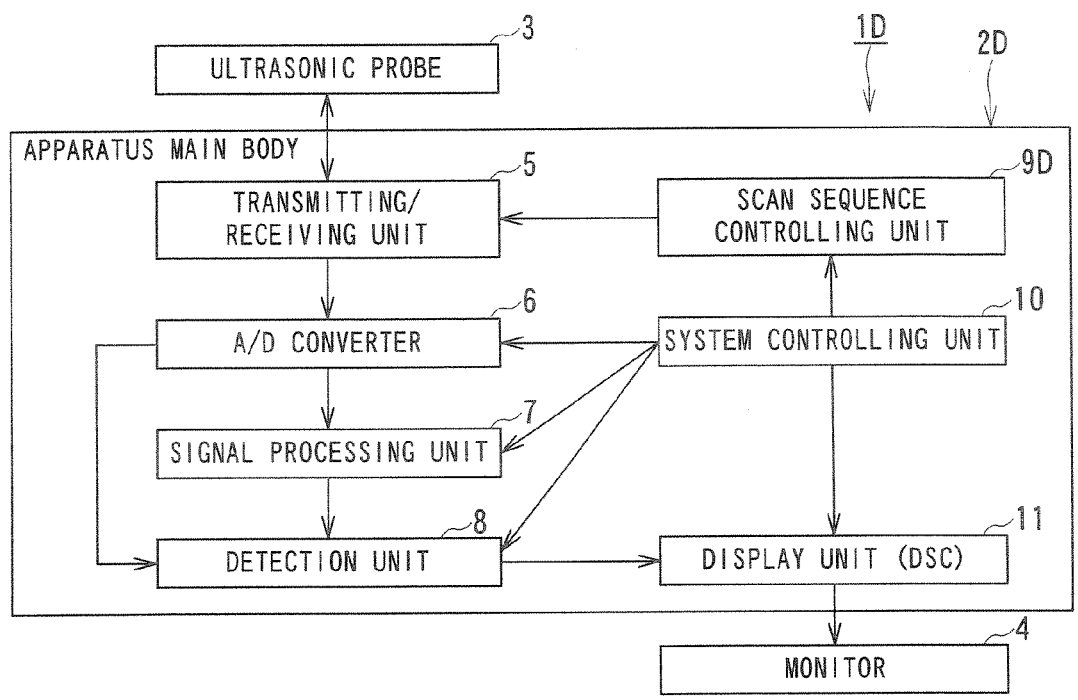
FIG. 25 is a diagram showing a configuration of an ultrasonic diagnostic apparatus according to a fifth embodiment of the present invention.

FIG. 25 is a diagram showing a configuration of an ultrasonic diagnostic apparatus according to a fifth embodiment of the present invention.

An ultrasonic diagnostic apparatus 1D according to the fifth embodiment is constituted by an apparatus main body 2D, an ultrasonic probe 3, and a monitor 4. The apparatus main body 2D has a transmitting/receiving unit 5, an A/D converter 6, a signal processing unit 7, a detection unit 8, a scan sequence controlling unit 9D, a system controlling unit 10, and a display unit 11. Each unit in the apparatus main body 2D may be implemented by circuits or by a CPU of a computer loading a control program. The ultrasonic diagnostic apparatus 1D is assumed to be used for convex scan and linear scan. The same units in the ultrasonic diagnostic apparatus 1D shown in FIG. 25 as those in the ultrasonic diagnostic apparatus 1 shown in FIG. 1 are denoted by the same numerals, and description thereof is omitted.

Compared with the scan sequence controlling unit 9, the scan sequence controlling unit 9D employs different usage of the ultrasonic probe 3 and different ultrasonic pulses to be transmitted. In addition, as for the ultrasonic diagnostic apparatus 1D, a combination with at least one is possible among the ultrasonic diagnostic apparatus 1A and 1B.

An operation of the ultrasonic diagnostic apparatus 1D is substantially the same as that of the ultrasonic diagnostic apparatus 1 shown in FIG. 1, the ultrasonic diagnostic apparatus 1A, or the ultrasonic diagnostic apparatus 1B except for the usage of the ultrasonic probe 3 and the ultrasonic pulses to be transmitted.

FIGS. 26 and 27 are diagrams illustrating a method for transmitting the ultrasonic pulses employed by the ultrasonic diagnostic apparatus 1D shown in FIG. 25.

As shown in FIGS. 26 and 27, in the ultrasonic diagnostic apparatus 1D, ultrasonic pulses p6 and p7 are assigned alternatively to each ultrasonic transducer group of the ultrasonic probe 3 having a predetermined number of ch (channels) (e.g., 16 ch). However, it is preferable for the transmission apertures of the ultrasonic probe 3 to be divided into a plurality of groups that assume the ultrasound transducers that does not overlap each other.

FIG. 26 is a diagram illustrating a case where a transmission beam (or a reception beam) is formed by transmission aperture groups, which are set independently of the number of channels of the ultrasonic transducer group. When a reception beam R is formed by the transmission aperture groups A and B (e.g., 20 ch for both group), a ratio of the ultrasonic pulse p6 to the ultrasonic pulse p7 differs between a reception beam RA received by the transmission aperture group A and a reception beam RB received by the transmission aperture group B. Thus, if the reception beams RA and RB are formed from the ultrasonic pulse p1 (or the ultrasonic pulse p2) transmitted by the ultrasonic diagnostic apparatus 1, a nonlinear effect and the degree of the saturation are different.

On the other hand, FIG. 27 shows transmission aperture groups used by the ultrasonic diagnostic apparatus 1D. More specifically, FIG. 27 is a diagram illustrating a case where a transmission beam (a reception beam) is formed by a transmission aperture group, whose number of channels is set at positive even times of the number of channels of the ultrasonic transducer group. When the reception beam R is formed by the transmission aperture groups A and B (e.g., 32 ch for both groups), the ratio of the ultrasonic pulse p6 to the ultrasonic pulse p7 agrees between the reception beam RA received by the transmission aperture group A and the reception beam RB received the transmission aperture group B.

Figure 28A:
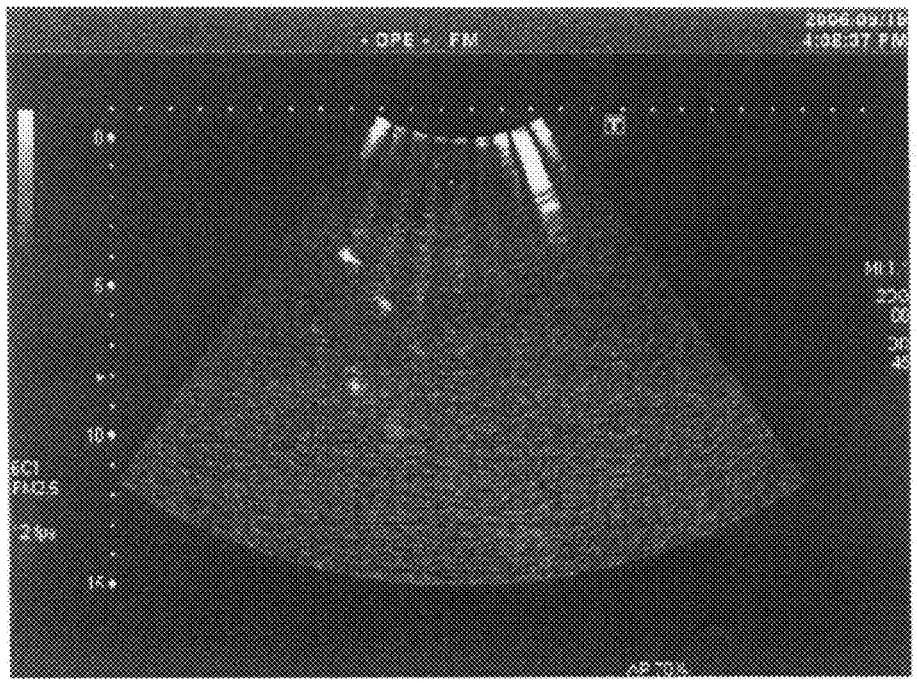
FIG. 28 is a diagram illustrating an ultrasonographic image generated by the ultrasonic diagnostic apparatus shown in FIG. 25.
Figure 28B:
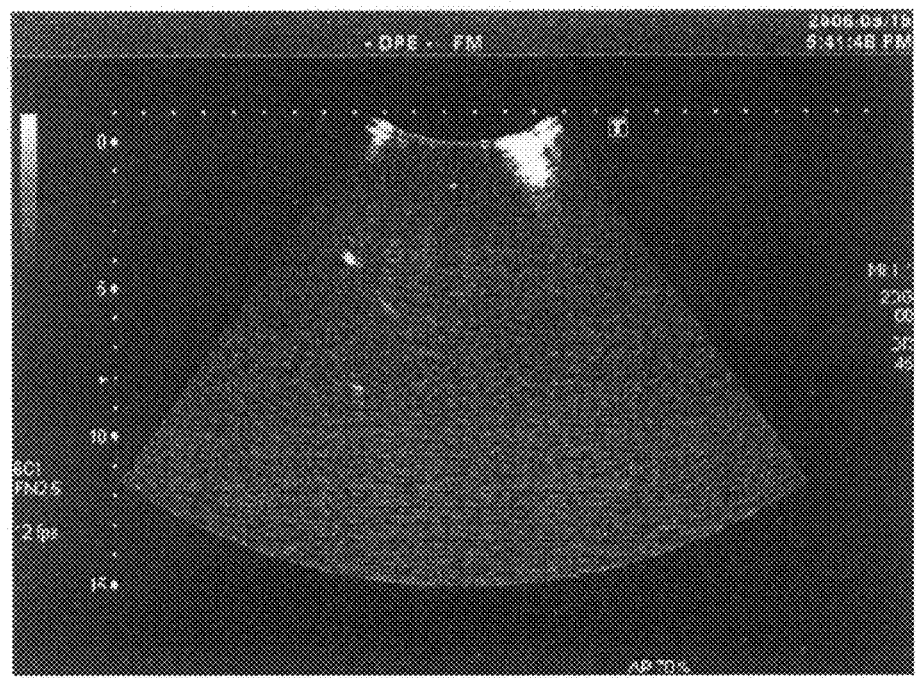

FIG. 28 is a diagram illustrating an ultrasonographic image generated by the ultrasonic diagnostic apparatus 1D shown in FIG. 25.

The upper diagram of FIG. 28 shows an ultrasonographic image generated by the transmission apertures whose group is set independently of the number of channels of the ultrasonic transducer group as shown in FIG. 26. On the other hand, the lower diagram of FIG. 28 shows an ultrasonographic image generated by the transmission apertures whose group is set at double of the number of channels of the ultrasonic transducer group as shown in FIG. 27.

Compared with the ultrasonographic image of the upper diagram of FIG. 28, in the ultrasonographic image of the lower diagram of FIG. 28, the degree of the nonlinear effect and of the saturation are suppressed, and an intensity of vertical lines appeared on the ultrasonographic image is decreased.

According to the ultrasonic diagnostic apparatus 1D and the ultrasonic diagnostic method according to the embodiment, the ultrasonic echoes reflected from the tissue of the living body are suppressed and the ultrasonic echoes reflected from more bubbles having different radiuses are visualized, thereby allowing easy recognition of the contrast enhancement by the bubbles at a higher sensitivity.

In addition, according to the ultrasonic diagnostic apparatus 1D and the ultrasonic diagnostic method according to the embodiment, by setting the ratio of the ultrasonic transducers, in the transmission aperture, that transmit the ultrasonic pulse p1 to the ultrasonic transducers that transmit the ultrasonic pulse p2 at a constant value, the intensity of vertical lines appeared on the ultrasonographic image can be decreased.

What is claimed is:

1. An ultrasonic diagnostic apparatus, comprising:
an ultrasonic probe;
a transmitter/receiver configured to transmit, after a contrast medium is injected to an object, by the ultrasonic probe, a first ultrasonic pulse and a second ultrasonic pulse that have different center frequency from each other, and a third ultrasonic pulse that has corresponding frequency component characteristics resulting from a combined pulse obtained by combining the first and second ultrasonic pulses, wherein the first, second, and third ultrasonic pulses are transmitted to the object one after another, and to receive, by the ultrasonic probe, each of reception echoes corresponding to the ultrasonic pulses;
a signal processor configured to process the reception echoes corresponding to the first, second, and third ultrasonic pulses, and to generate a processed signal; and
an image generating processor configured to generate a contrast image by use of the processed signal.

2. The ultrasonic diagnostic apparatus according to claim 1, wherein the transmitter/receiver generates the first and second ultrasonic pulses by making at least one of an amplitude and a frequency band of the center frequency to be different.

3. The ultrasonic diagnostic apparatus according to claim 2, wherein the transmitter/receiver transmits the first and second ultrasonic pulses by making at least one of a phase, a functional ultrasonic transducer of a plurality of ultrasonic transducers included in the ultrasonic probe, and a transmission focus for each of the ultrasonic pulses be different.

4. The ultrasonic diagnostic apparatus according to claim 3, wherein the transmitter/receiver performs phase inversion of a pulse of one of the first and second ultrasonic pulses.

5. The ultrasonic diagnostic apparatus according to claim 3, wherein the transmitter/receiver controls the ultrasonic probe so that a number of the functional ultrasonic transducers is set to an integral multiple more than twice a number of ultrasonic transducers of an ultrasonic transducer group.

6. The ultrasonic diagnostic apparatus according to claim 5, wherein the transmitter/receiver controls the ultrasonic probe so that the number of the functional ultrasonic transducers is set to twice the number of the ultrasonic transducers of the ultrasonic transducer group.

7. The ultrasonic diagnostic apparatus according to claim 1, wherein the transmitter/receiver sets the first and second ultrasonic pulses, and each frequency band of the ultrasonic pulses does not overlap each other.

8. The ultrasonic diagnostic apparatus according to claim 7, wherein the center frequency of one of the first and second ultrasonic pulses is set to an integer multiple not less than double of the other.

9. The ultrasonic diagnostic apparatus according to claim 1, wherein the signal processor adds the reception echoes corresponding to the first and second ultrasonic pulses and subtracts the reception echo corresponding to the third ultrasonic pulse from the added reception echo.

10. The ultrasonic diagnostic apparatus according to claim 1, wherein the signal processor corrects amplitudes of the reception echoes corresponding to the first, second, and third ultrasonic pulses in accordance with amplitudes of the first, second, and third ultrasonic pulses.

11. The ultrasonic diagnostic apparatus according to claim 1, wherein the signal processor corrects phases of the reception echoes corresponding to the first, second, and third ultrasonic pulses in accordance with phases of the first, second, and third ultrasonic pulses.

12. The ultrasonic diagnostic apparatus according to claim 1, further comprising:
 a tissue image generating processor configured to generate a B mode image as a tissue image of the object by use of at least one of the reception echoes corresponding to the first and second ultrasonic pulses and the reception echo corresponding to the third ultrasonic pulse; and
 a display configured to display both the contrast image and the tissue image on a monitor.

13. The ultrasonic diagnostic apparatus according to claim 1, wherein the transmitter/receiver transmits the third ultrasonic pulse having a transmission sound field formed from transmission sound fields of the first and second ultrasonic pulses so that the third ultrasonic pulse has the same frequency component characteristics as the combined pulse.

14. The ultrasonic diagnostic apparatus according to claim 13, wherein the transmitter/receiver transmits the first and second ultrasonic pulses by switching an ultrasonic transducer group of one of the first and second ultrasonic pulses to the other, and transmits the third ultrasonic pulse by combining the ultrasonic transducer groups of the first and second ultrasonic pulses, if a plurality of ultrasonic transducers included in the ultrasonic probe are categorized into two ultrasonic transducer groups.

15. An ultrasonic diagnostic method, comprising:
 transmitting, after a contrast medium is injected to an object, by an ultrasonic probe transmit, a first ultrasonic pulse and a second ultrasonic pulse that have different center frequency from each other, and a third ultrasonic pulse that has corresponding frequency component characteristics resulting from a combined pulse obtained by combining the first and second ultrasonic pulses, wherein the first, second, and third ultrasonic pulses are transmitted to the object one after another;
 receiving at the ultrasonic probe each of reception echoes corresponding to the ultrasonic pulses;
 processing reception echoes for processing the reception echoes corresponding to the first, second, and third ultrasonic pulses, and generating a processed signal; and
 generating an image for generating a contrast image by use of the processed signal.

16. The ultrasonic diagnostic method according to claim 15, wherein the transmitting transmits the first and second ultrasonic pulses by making at least one of an amplitude and a frequency band of the center frequency to be different.

17. The ultrasonic diagnostic method according to claim 16, wherein the transmitting transmits the first and second ultrasonic pulses by making at least one of a phase, a functional ultrasonic transducer of a plurality of ultrasonic transducers included in the ultrasonic probe, and a transmission focus for each of the ultrasonic pulses be different.

18. The ultrasonic diagnostic method according to claim 17, wherein the transmitting performs phase inversion of a pulse of one of the first and second ultrasonic pulses.

19. The ultrasonic diagnostic method according to claim 17, wherein the transmitting controls the ultrasonic probe so that the number of the functional ultrasonic transducers is set to an integral multiple more than twice the number of ultrasonic transducers of an ultrasonic transducer group.

20. The ultrasonic diagnostic method according to claim 19, wherein the transmitting controls the ultrasonic probe so that the number of the functional ultrasonic transducer is set to double of the number of the ultrasonic transducers of the ultrasonic transducer group.

21. The ultrasonic diagnostic method according to claim 15, wherein the transmitting sets the first and second ultrasonic pulses, and each frequency band of the ultrasonic pulses does not overlap each other.

22. The ultrasonic diagnostic method according to claim 21, wherein the center frequency of one of the first and second ultrasonic pulses is set to an integer multiple not less than double of the other.

23. The ultrasonic diagnostic method according to claim 15, wherein the processing reception echoes adds the reception echoes corresponding to the first and second ultrasonic pulses and subtracts the reception echo corresponding to the third ultrasonic pulse from the added reception echo.

24. The ultrasonic diagnostic method according to claim 15, wherein the processing reception echoes corrects amplitudes of the reception echoes corresponding to the first, second, and third ultrasonic pulses in accordance with amplitudes of the first, second, and third ultrasonic pulses.

25. The ultrasonic diagnostic method according to claim 15, wherein the processing reception echoes corrects phases of the reception echoes corresponding to the first, second, and third ultrasonic pulses in accordance with phases of the first, second, and third ultrasonic pulses.

26. The ultrasonic diagnostic method according to claim 15, further comprising:
 generating tissue image for generating a tissue image of the object by use of at least one of the reception echoes corresponding to the first and second ultrasonic pulses and the reception echo corresponding to the third ultrasonic pulse; and
 displaying both the contrast image and the tissue image on a monitor.

27. The ultrasonic diagnostic method according to claim 15, wherein the transmitting transmits the third ultrasonic pulse having a transmission sound field formed from transmission sound fields of the first and second ultrasonic pulses so that the third ultrasonic pulse has the same frequency component characteristics as the combined pulse.

28. The ultrasonic diagnostic method according to claim 27, wherein the transmitting transmits the first and second ultrasonic pulses by switching an ultrasonic transducer group of one of the first and second ultrasonic pulses to the other, and transmits the third ultrasonic pulse by combining the ultrasonic transducer groups of the first and second ultrasonic pulses, if a plurality of ultrasonic transducers included in the ultrasonic probe are categorized into two ultrasonic transducer groups.

* * * * *